United States Patent
Wu et al.

(10) Patent No.: US 11,046,720 B2
(45) Date of Patent: Jun. 29, 2021

(54) DIMETHYLPHOSPHINE OXIDE COMPOUND

(71) Applicant: GUIZHOU INOCHINI TECHNOLOGY CO., LTD, Guiyang (CN)

(72) Inventors: Lingyun Wu, Shanghai (CN); XiaWei Wei, Sichuan (CN); Peng Zhang, Shanghai (CN); Zhaoguo Chen, Shanghai (CN); Cailin Wang, Shanghai (CN); Lele Zhao, Shanghai (CN); Jian Li, Shanghai (CN); Shuhui Chen, Shanghai (CN)

(73) Assignee: GUIZHOU INOCHINI TECHNOLOGY CO., LTD, Guiyang (CN)

( * ) Notice: Subject to any disclaimer, the term of this patent is extended or adjusted under 35 U.S.C. 154(b) by 0 days.

(21) Appl. No.: 17/048,951

(22) PCT Filed: Apr. 19, 2019

(86) PCT No.: PCT/CN2019/083462
§ 371 (c)(1),
(2) Date: Oct. 19, 2020

(87) PCT Pub. No.: WO2019/201334
PCT Pub. Date: Oct. 24, 2019

(65) Prior Publication Data
US 2021/0147453 A1    May 20, 2021

(30) Foreign Application Priority Data
Apr. 20, 2018  (CN) .......................... 201810360120.0

(51) Int. Cl.
*C07F 9/53* (2006.01)

(52) U.S. Cl.
CPC .................................. *C07F 9/5325* (2013.01)

(58) Field of Classification Search
CPC ..................................................... C07F 9/5325
USPC .......................................................... 514/86
See application file for complete search history.

(56) References Cited

FOREIGN PATENT DOCUMENTS

| CN | 103501612 A | 1/2014 | |
|----|-------------|--------|----|
| CN | 109369721 A | 2/2019 | |
| WO | 2013169401 A1 | 11/2013 | |
| WO | WO-2017086832 A1 * | 5/2017 | ........... C07D 487/10 |

OTHER PUBLICATIONS

International Search Report for International Application No. PCT/CN2019/083462, dated 2019.
Written Opinion of International Search Authority for International Application No. PCT/CN2019/083462, dated 2019.

* cited by examiner

*Primary Examiner* — Kristin A Vajda
(74) *Attorney, Agent, or Firm* — JCIP; Joseph G. Chu; Jeremy I. Maynard

(57) ABSTRACT

Disclosed is an application of a series of dimethylphosphine oxide compounds in the preparation of an LRRK2 kinase activity inhibitor-related drug, specifically an application of the compound shown in formula (I) or a pharmaceutically acceptable salt thereof in the preparation of an LRRK2 kinase activity inhibitor-related drug.

12 Claims, 1 Drawing Sheet

DIMETHYLPHOSPHINE OXIDE COMPOUND

Figure 1:
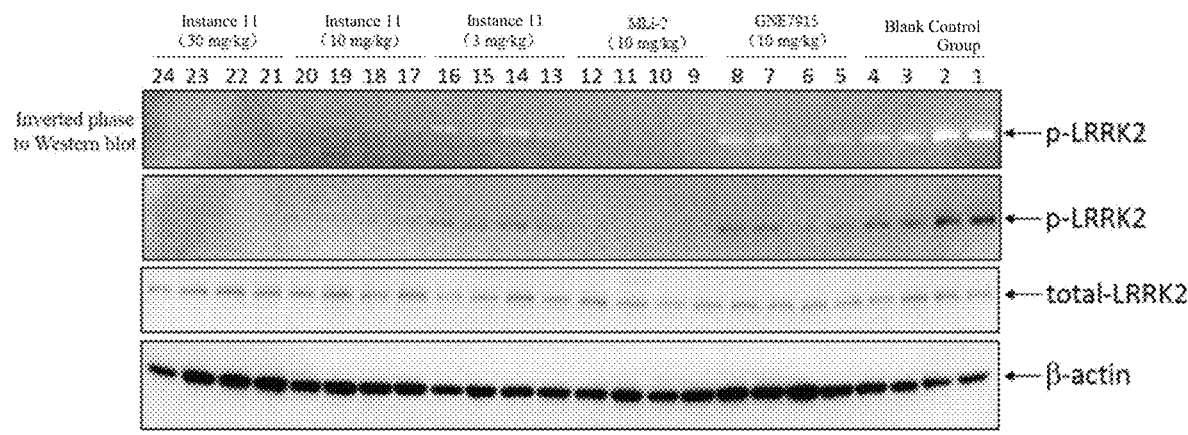

This application claims the following priorities:
CN 201810360120.0, application date: 20 Apr. 2018

TECHNICAL FIELD

This invention involves applications of a series of dimethylphosphine oxide compounds in the preparation of an LRRK2 kinase activity inhibitor-related drug, specifically the application of the compound shown in formula (I) or a pharmaceutically acceptable salt thereof in the preparation of an LRRK2 kinase activity inhibitor-related drug.

BACKGROUND TECHNOLOGIES

An increasing number of evidences have shown that mutation and over-expression of LRRK2 is a root cause of neurodegenerative diseases, mainly featuring selective degeneration and cell death of dopaminergic neurons in substantia nigra. These diseases impact 1% people older than 65, 5-10% of whom are hereditary patients. In the early stage of the diseases, the most evident symptoms are tremor, slow movement and walking difficulty. In the later stage of the diseases, patients will have cognitive and behavioral problems. Patients in the advanced stage will suffer from dementia.

More and more evidences suggest that mutation of leucine-rich repeat kinase 2 (LRRK2) is inseparably associated with neurodegenerative disease. LRRK2 is a 2527-amino acid protein involved in catalytic phosphorylation and GTP-GDP hydrolysis. NM_198578.2 is the NCBI sequence of human LRRK2 mRNA. Some evidences demonstrate that LRRK2 phosphorylates alpha-synuclein at serine-129, and this form of phosphorylation is an integral part of Lewy body. In addition, some evidences show that single nucleotide polymorphism in the functional domain of LRRK2 causes common and sporadic neurodegenerative diseases. So far, researchers have identified more than 20 LRRK2 mutations in families with delayed neurodegenerative diseases. For instance, G2019S mutation is co-segregated with autosomal dominant. Due to the mutation, there are approximately 6% familial cases and 3% sporadic cases in Europe. G2019S mutation occurs in the highly conserved domain of kinase, so it might affect kinase activity. In addition, amino acid substitutions in another residue R1441 are also related to neurodegenerative diseases, and suggested to increase the LRRK2 kinase activity. The over-expression of R1441G in the mutant LRRK2 of the transgenic mouse model is correlated to release of less dopamine. It is demonstrated that LRRK2 inhibitor actively regulates release of dopamine, with potential efficacy for treating diseases characterized by declined dopamine level. According to relevant data, LRRK2 kinase activity inhibitor can be also used for treating related neurodegenerative diseases.

Therefore, developing potent inhibitors of LRRK2 and its mutants is one important way for treating neurodegenerative diseases. This invention aims to invent a compound for highly inhibiting LRRK2, in order to further invent potent drugs for treating neurodegenerative diseases.

ACS Med. Chem. Lett. (2015, 6, 584-589) published the compound JH-II-127, which is LRRK2 kinase activity inhibitor, and the structural formula of this compound is as follows:

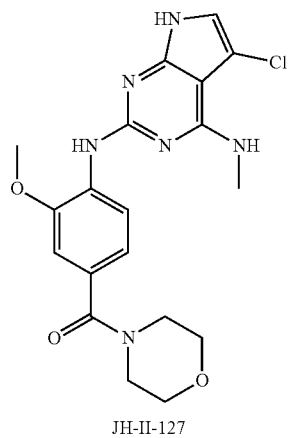 [SMILES: CNc1nc(Nc2ccc(C(=O)N3CCOCC3)cc2OC)nc2[nH]cc(Cl)c12]

JH-II-127

J Med. Chem. (2012, 55, 9416-9433) also publicized the compound GNE-7915, which is a LRRK2 kinase activity inhibitor, with a structural formula as follows:

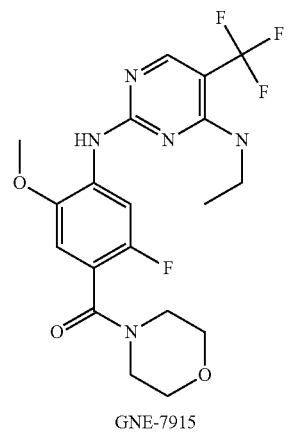 [SMILES: CCNc1nc(Nc2cc(F)c(C(=O)N3CCOCC3)cc2OC)ncc1C(F)(F)F]

GNE-7915

Content of the Invention

This invention provides the compound shown in formula (I) and its pharmaceutically acceptable salt.

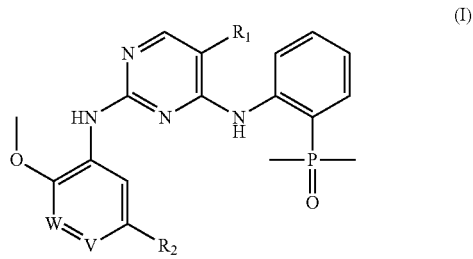

Wherein:
$R_1$ is selected from halogen, OH, $NH_2$ and $C_{1-6}$ alkyl, wherein the alkyl is optionally substituted by 1, 2 or 3 $R_a$ radicals;
W is selected from N; V is selected from $C(R_3)$;
Or W is selected from $C(R_3)$; V is selected from N;
$R_2$ is selected from H; $R_3$ is selected from

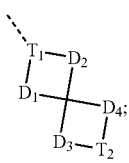

Or $R_2$ is selected from

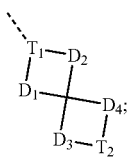

$R_3$ is selected from H;

$T_1$ is selected from N and CH;

$T_2$ is selected from —O—, —CH$_2$— and —CH$_2$CH$_2$—, wherein —CH$_2$— is optionally substituted by 1 or 2 $R_b$ radicals; —CH$_2$CH$_2$— is optionally substituted by 1, 2 or 3 $R_b$ radicals;

$D_1$ and $D_2$ are separately selected from single bonds, —CH$_2$— and —CH$_2$CH$_2$—, wherein —CH$_2$— is optionally substituted by 1 or 2 $R_c$ radicals; —CH$_2$CH$_2$— is optionally substituted by 1, 2 or 3 $R_c$ radicals; $D_1$ and $D_2$ are not simultaneously selected from single bonds;

$D_3$ and $D_4$ are separately selected from single bonds, —O—, —CH$_2$— and —CH$_2$CH$_2$—, wherein —CH$_2$— is optionally substituted by 1 or 2 $R_d$ radicals, and —CH$_2$CH$_2$— is substituted by 1, 2 or 3 $R_d$ radicals. $D_3$ and $D_4$ are not simultaneously selected from single bonds;

$R_a$ is separately selected from F, Cl, Br, I, OH and NH$_2$;

$R_b$ is separately selected from F, Cl, Br, I, OH and NH$_2$;

$R_c$ is separately selected from F, Cl, Br, I, OH and NH$_2$;

$R_d$ is separately selected from F, Cl, Br, I, OH, NH$_2$, C$_{1-6}$ alkyl and C$_{1-6}$ heteroalkyl, wherein C$_{1-6}$ alkyl and C$_{1-6}$ heteroalkyl are optionally substituted by 1, 2 or 3 R radicals;

R is separately selected from F, Cl, Br, I, OH and NH$_2$;

C$_{1-6}$ heteroalkyl contains 1, 2 or 3 heteroatoms and heteroatom clusters of —O—, —S— and —NH—.

In some embodiments of this invention, $R_1$ is selected from F, Cl, Br, I, OH, NH$_2$ and C$_{1-3}$ alkyl, wherein C$_{1-3}$ alkyl is optionally substituted by 1, 2 or 3 $R_a$ radicals. Other variables have the meanings as defined in this invention.

In some embodiments of this invention, $R_1$ is selected from F, Cl, Br, I, OH, NH$_2$ and CF$_3$. Other variables have the meanings as defined in this invention.

In some embodiments of this invention, $D_1$ and $D_2$ are separately selected from single bonds, —CH$_2$— and —CH$_2$CH$_2$—. D1 and D2 are not simultaneously selected from single bonds, while other variables have the meanings as defined in this invention.

In some embodiments of this invention, $R_d$ is separately selected from F, Cl, Br, I, OH, NH$_2$, C$_{1-3}$ alkyl and C$_{1-3}$ oxyalkyl, wherein C$_{1-3}$ alkyl and C$_{1-3}$ oxyalkyl are optionally substituted by 1, 2 or 3 R radicals. Other variables have the meanings as defined in this invention.

In some embodiments of this invention, $R_d$ is separately selected from F, Cl, Br, I, OH, NH$_2$, C$_{1-3}$ alkyl and C$_{1-3}$ oxyalkyl. Other variables have the meanings as defined in this invention.

In some embodiments of this invention, $R_d$ is separately selected from F, Cl, Br, I, OH, NH$_2$, Me, CF$_3$ and

Other variables have the same meanings as defined in this invention.

In some embodiments of this invention, $D_3$ and $D_4$ are separately selected from single bonds, —O—, —CH$_2$—, CF$_2$—, —CH$_2$CF$_2$— and

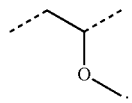

$D_3$ and $D_4$ are selected from single bonds, and other variables have the same meanings as defined in this invention.

In some embodiments of this invention,

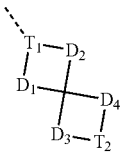

is selected from

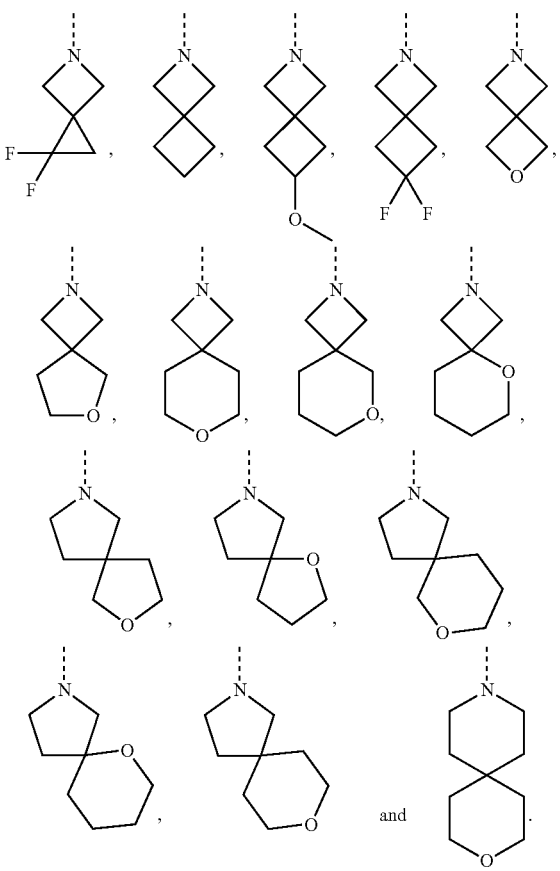

Other variables have the same meanings as defined in this invention.

In some embodiments of this invention, the compound or its pharmaceutically acceptable salts is selected from
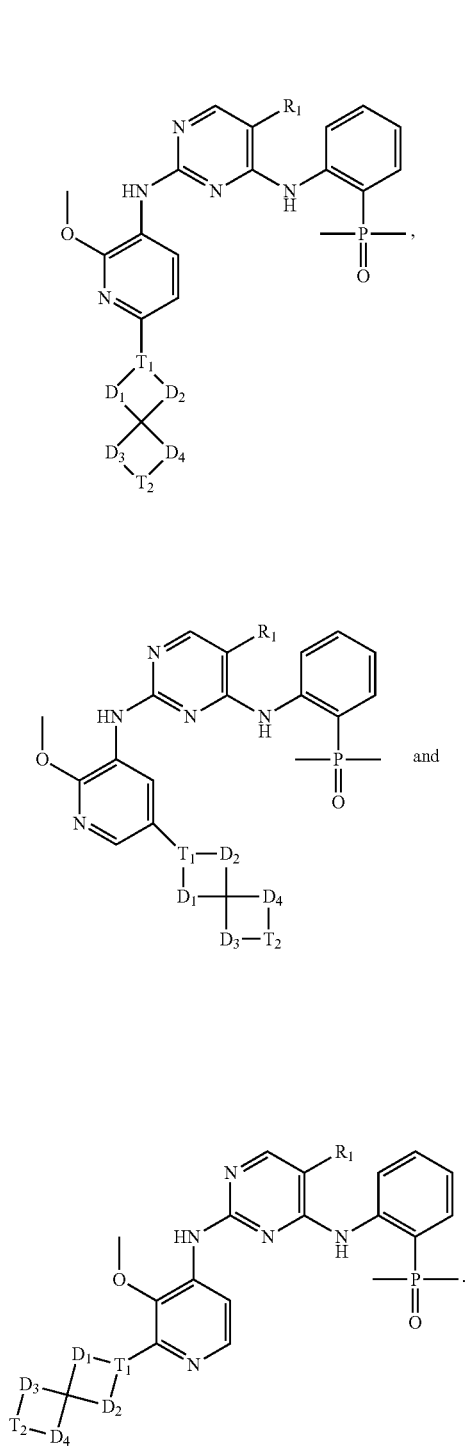
Wherein:
R₁, T₁, T₂, D₁, D₂, D₃ and D₄ have the meanings as defined above.
Some embodiments of this invention are random combinations of the variables.
In addition, this invention provides the following compound or its pharmaceutically acceptable salt:
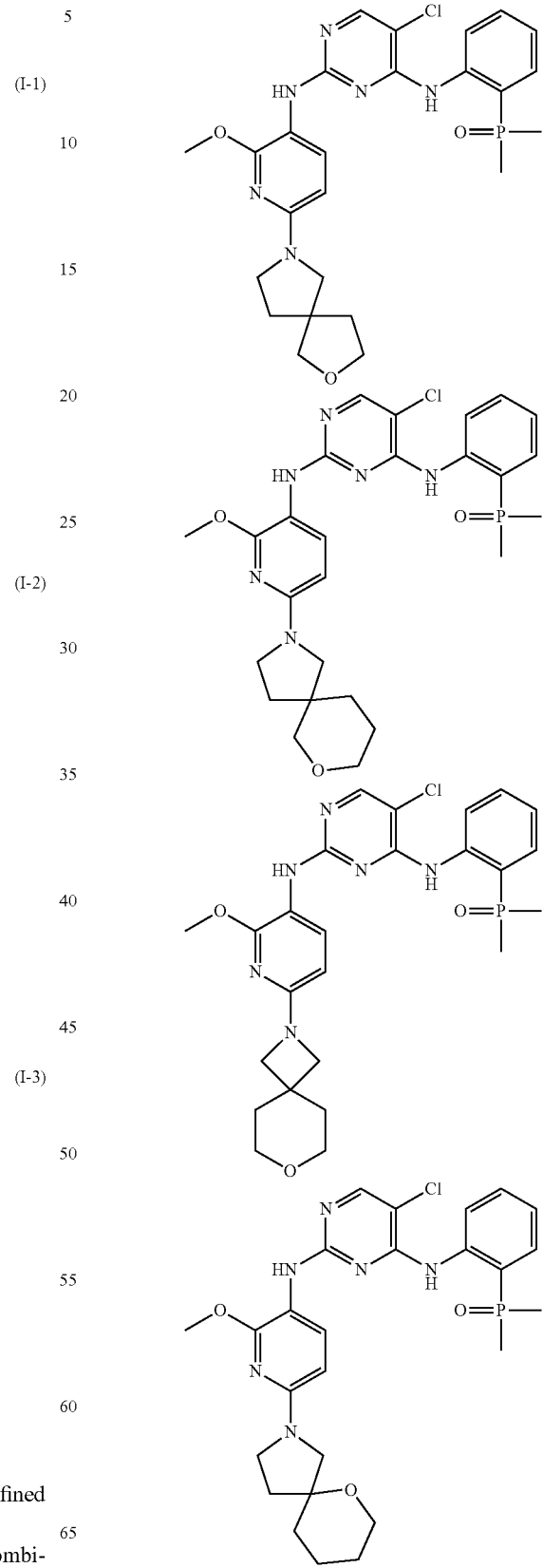

-continued
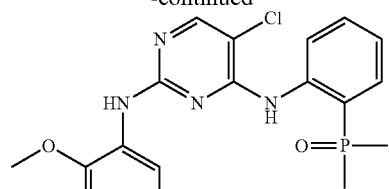
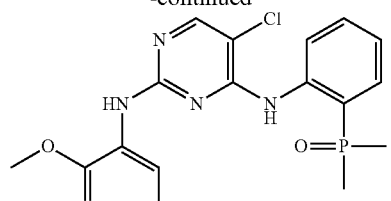
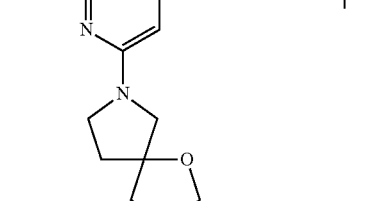
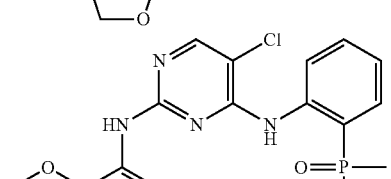
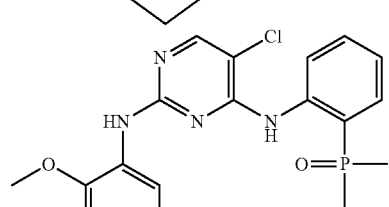
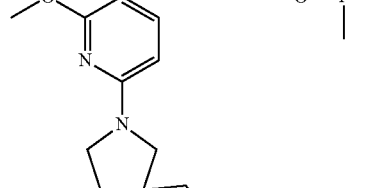
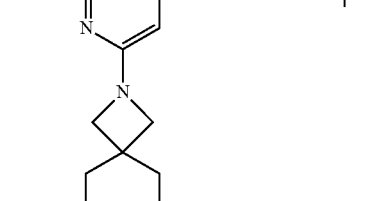
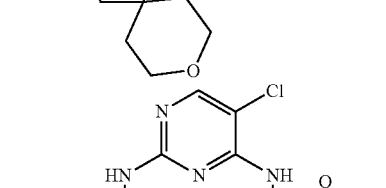
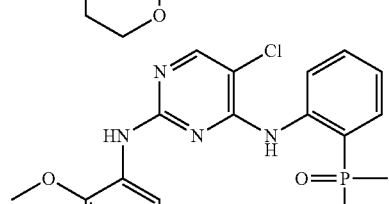
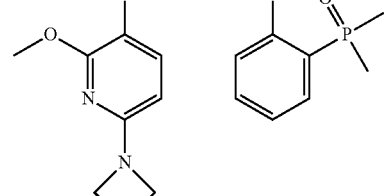
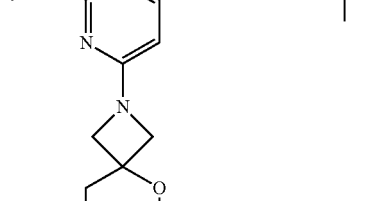
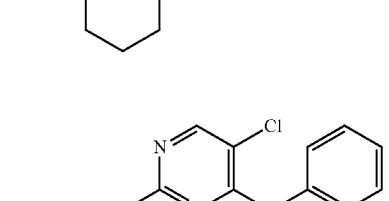
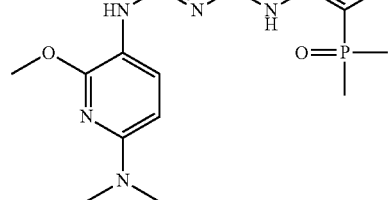
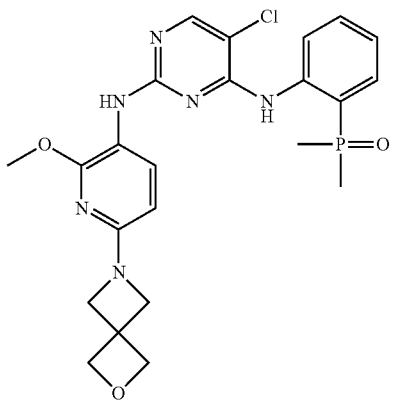
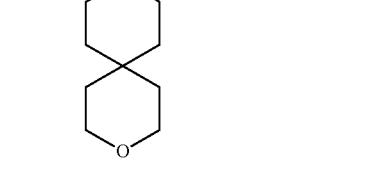

-continued
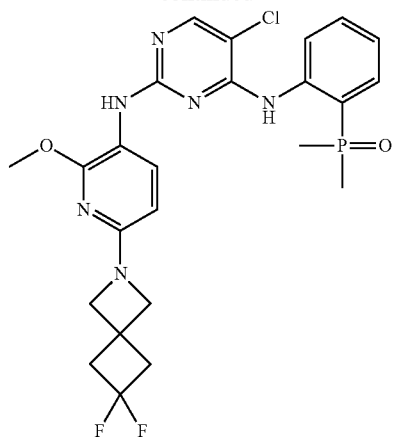
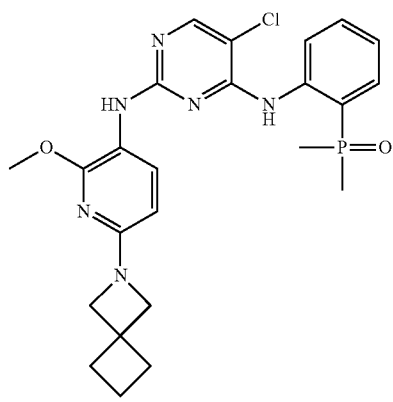
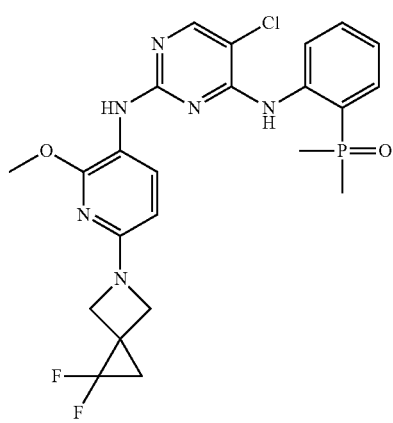
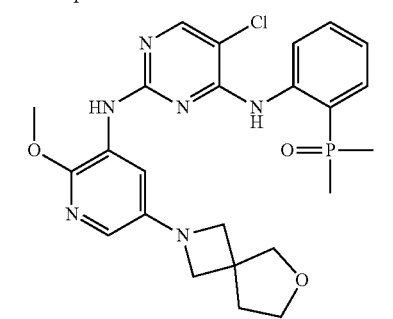
-continued
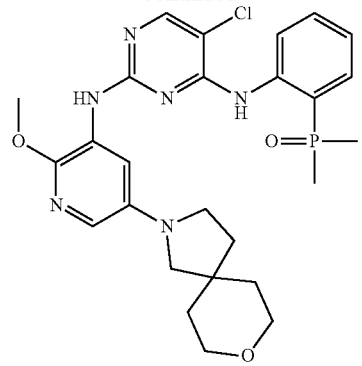
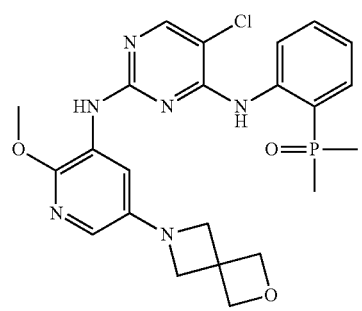
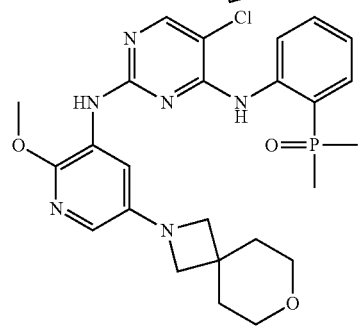
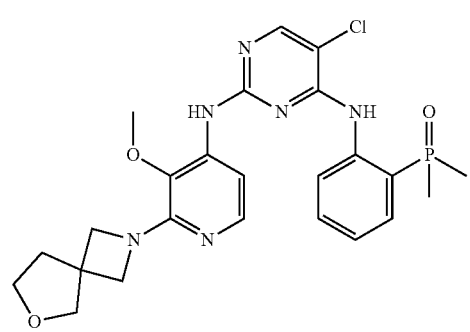
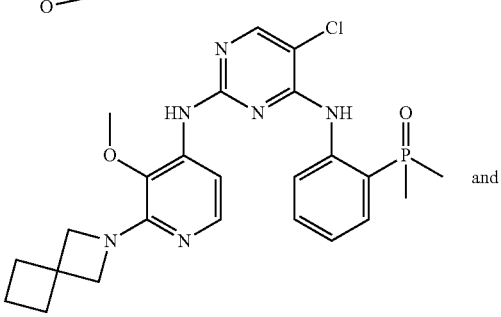 and -continued

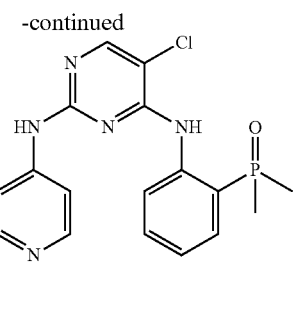

Besides, this invention specifies the applications of the compound or the pharmaceutically acceptable salt thereof in LRRK2 kinase activity inhibitor-related drugs.
Technical Efficacy The compound in this invention, with potent efficacy for LRRK2 kinase activity inhibition and high cell viability, is quite dialytic and soluble. Meanwhile, it exhibits superior pharmacokinetic and pharmacodynamic properties.

Definitions and Descriptions

Definitions and Interpretations

Unless otherwise specified, terms and phrases of this paper shall have following meanings. A specific term or phrase, if not specially defined, shall not be deemed uncertain or indefinite, but shall be understood according to their general meanings. The commodities mentioned hereunder shall mean corresponding commodities or their active ingredients. "Pharmaceutically acceptable" is a term specific to compounds, materials, compositions and/or dose forms within the range of reliable medical judgment, which are suitable for tissue exposure and application in the mankind and animals without over high toxicity, irritation, hypersensitivity or other problems or complications, commensurate with the appropriate reward to risk ratio.

"Pharmaceutically acceptable salt" means salt of an invented compound, prepared by the compound with specific substitute groups discovered in this invention and relatively nontoxic acid or alkali. When a compound of this invention contains relatively acid functional groups, the salt thereof can be prepared by making an enough amount of alkali in contact with the neutral form of the invented compound in pure solution or suitable inert solvent. Alkali-formed salt includes sodium salt, potassium, calcium, ammonium, organic amine or magnesium salt or similar salt. When the invented compound has relatively alkaline functional groups, salt can be prepared by making an adequate amount of acid in contact with the neutral form of the compound in pure solution or suitable inert solvent. Pharmaceutically acceptable acid-formed salt includes inorganic acid salt (inorganic acid hereby mentioned includes hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid and phosphorous acid), organic acid salt (organic acid hereby mentioned includes acetic acid, propanoic acid, isobutyric acid, maleic acid, propanedioic acid, benzoic acid, succinic acid, suberic acid, fumaric acid, lactic acid, mandelic acid, phthalic acid, benzenesulfonic acid, P-toluenesulfonic acid, citric acid, tartaric acid, methanesulfonic acid and similar acid), amino acid (e.g. arginine) and organic acid (e.g. glucuronic acid) salt. Certain specific compounds in this invention contain some alkali and acid functional groups, which can be converted into any alkali or acid-forming salt.

The pharmaceutically acceptable salt in this invention can be synthesized with parented compound containing acidic groups or nucleobases by routine chemical methods. Generally, such salt is prepared as follows: the compound existing in the form of free acid or alkaline reacts with chemically appropriate alkaline or acid in water or organic solvent or mixture of water and organic solvent.

One or more atoms constituting the invented compound may contain atomic isotopes at a non-natural ratio. For example, the compound can be labeled with radioactive isotopes such as $^3H$, $^{125}I$ or C-14 ($^{14}C$). Furthermore, heavy hydrogen may substitute for hydrogen to prepare deuterium-substituted drugs. The bonds composed by deuterium and carbon are firmer than those made up of carbon. Deuterium-substituted drugs outperform non-deuterated drugs due to its advantages for reducing poisonous side effects, increasing drug stability, enhancing therapeutic efficacy and prolonging biological half-life of drugs. All conversions from isotopes of the invented compound are within the scope of this invention no matter they are radioactive or not.

"Optional" or "optionally" means the events or circumstances described thereafter are probable but will unnecessarily occur, and includes the situations of such events or circumstances that will or will not occur.

"Substituted" means that any one or more hydrogen atoms are replaced by substituent groups on certain atom. The substituent groups may include heavy hydrogen and hydrogen variants as long as the valence of the atoms is normal and the compound is stable after the substitution. "Optionally substituted" means the mentioned may be substituted or not be substituted. Unless otherwise specified, type and quantity of the substituent groups may be optional if only the substitution is chemically possible.

When any variable (e.g. R) occurs more than once in the composition or structure of the compound, its definition under each situation shall be independent. Therefore, if one radical group is substituted by 0 to 2 R radicals, the radical group may be optionally substituted by two R radicals at most, and under each situation, there is an independent option for R. in addition, only if the combination of the substituent group and/or its variant produces a stable compound will it be allowable.

When a variable is selected from a single bond, the two radical groups connected by this variable will be directly connected. For instance, if L in A-L-Z is a single bond, the structure, in essence, is A-Z.

If it is uncertain through which atom that the exemplified substituent group is connected to the substituted radical group, the substituent group may be bonded to the substituted one through any of its atoms. For instance, pyridine group, as the substituent group, may be connected to the substituted radical group via any carbon atom on the pyridine ring.

Unless otherwise specified, "$C_{1-6}$ alkyl" refers to saturated chloridated carbon groups of a straight chain or branched chain with 1, 2, 3, 4, 5 or 6 carbon atoms. In some embodiments, $C_{1-6}$ alkyl includes $C_{1-6}$ alkyl, $C_{1-5}$ alkyl, $C_{1-4}$ alkyl, $C_{1-3}$ alkyl, methyl (Me), ethyl (Et), propyl (including n-propyl and isopropyl), butyl (including n-butyl, isobutyl, s-butyl and t-butyl), amyl (including n-amyl, isoamyl and neoamyl) and hexyl and so on. It may have one valency (e.g. methyl), two valencies (e.g. methylene) or multiple valencies (e.g. methyne).

Unless otherwise specified, "$C_{1-3}$ alkyl alkyl" means carbon hydrogen groups of a straight chain or branched chain with 1, 2 or 3 carbon atoms. In some embodiments, $C_{1-3}$ alkyl includes $C_{1-3}$ alkyl, methyl (Me), ethyl (Et) and propyl (including n-propyl and isopropyl) and so on. It may have one valency (e.g. methyl), two valencies (e.g. methylene) or multiple valencies (e.g. methyne).

Unless otherwise specified, "$C_{1-6}$ heteroalkyl" means alkyl atomic groups of a stable straight chain or branched chain with 1, 2, 3, 4, 5 or 6 carbon atoms or at least composed of one heteroatom or heteroatom cluster. In some embodiments, it includes $C_{1-6}$ heteroalkyl, $C_{1-5}$ heteroalkyl, $C_{1-4}$ heteroalkyl, $C_{1-3}$ heteroalkyl, —$OCH_3$, —$OCH_2CH_3$, —$OCH_2CH_2CH_3$, —$OCH_2(CH_3)_2$, —$CH_2$—$CH_2$—O—$CH_3$, —$NHCH_3$, —$N(CH_3)_2$, —$NHCH_2CH_3$, —$N(CH_3)(CH_2CH_3)$, —$CH_2$—$CH_2$—NH—$CH_3$, —$CH_2$—$CH_2$—N($CH_3$)—$CH_3$, —$SCH_3$, —$SCH_2CH_3$, —$SCH_2CH_2CH_3$, —$SCH_2(CH_3)_2$ and —$CH_2$—S—$CH_2$—$CH_3$. The heteroatom or heteroatom cluster may be in any internal position of the heteroalkyl, including the position wherein the heteroalkyl is connected to other parts of the molecule. Two heteroatom clusters may be continuous at most (e.g. —$CH_2$—NH—$OCH_3$).

Unless otherwise specified, "$C_{1-3}$ heteroalkyl" means alkyl atomic groups of a stable straight chain or branched chain with 1, 2 or 3 carbon atoms and at least composed of one heteroatom or heteroatom cluster. In some embodiments, it includes $C_{1-3}$ heteroalkyl, —$OCH_3$, —$OCH_2CH_3$, —$OCH_2CH_2CH_3$, —$OCH_2(CH_3)_2$, —$CH_2$—$CH_2$—O—$CH_3$, —$NHCH_3$, —$N(CH_3)_2$, —$NHCH_2CH_3$, —$N(CH_3)(CH_2CH_3)$, —$CH_2$—$CH_2$—NH—$CH_3$, —$CH_2$—$CH_2$—N($CH_3$)—$CH_3$, —$SCH_3$, —$SCH_2CH_3$, —$SCH_2CH_2CH_3$, —$SCH_2(CH_3)_2$ and so on. The heteroatom or heteroatom cluster may be in any internal position of the heteroalkyl, including the position where the alkyl is connected to other parts of the molecule. Two heteroatom clusters may be continuous at most (e.g. —$CH_2$—NH—$OCH_3$).

"$C_{1-6}$ oxyalky", which is an idiomatic expression, means $C_{1-6}$ alkyl groups connected to other parts of the molecule through an oxygen atom. It includes $C_1$, $C_2$, $C_3$, $C_4$, $C_5$ and $C_6$ oxyalky. In some embodiments, $C_{1-6}$ oxyalky includes but not limited to $C_{1-6}$ oxyalky, $C_{1-5}$ oxyalky, $C_{1-4}$ oxyalky, $C_{1-3}$ oxyalky, methoxy, ethoxy, propoxy, isopropoxy, n-butoxy, sec-butoxy, tert-butoxy, n-pentyloxy and S-pentyloxy and so on.

"$C_{1-3}$ oxyalkyl", which is an idiomatic expression, means $C_{1-3}$ alkyl groups connected to other parts of the molecule through an oxygen atom, including $C_1$, $C_2$ and $C_3$ oxyalkyl. In some embodiments, $C_{1-6}$ oxyalkyl includes but not limited to $C_{1-3}$ oxyalkyl, methoxy, ethoxy, propoxy and isopropoxy and so on.

Unless otherwise specified, $C_{n-n+m}$ or $C_n$-$C_{n+m}$ may comprise of n to n+m carbon atoms. For example, $C_{1-6}$ includes $C_1$, $C_2$, $C_3$, $C_4$, $C_5$ and $C_6$. It may be also any one of n to n+m atoms. For instance, $C_{1-6}$ includes $C_{1-3}$, $C_{1-4}$, $C_{1-5}$, $C_{2-6}$, $C_{2-5}$ and $C_{2-4}$ and so on.

The compound in this invention may be prepared by multiple synthesis methods that technicians of this field are familiar with, including the specific methods exemplified below, their combination with other chemical synthesis methods and equivalent alternatives that technicians of this field are familiar with. The preferred options include but not limited to those adopted in this invention.

The solvent used in this invention is available from market. In this invention, following abbreviations are used: $CDCl_3$ (deuterated chloroform), $CD_3OD$ (methanol-D4), and DMSO-$d_6$ (dimethyl sulfoxide-$d_6$).

The compound is named according to the common naming principle of this field or with ChemDraws software. The compounds available from market are named as those shown in the suppliers' catalogues.

DESCRIPTIONS OF ATTACHED DRAWINGS

The 1$^{st}$ attached drawing shows the western blot results on immunity of brain tissues.

The 2$^{nd}$ attached drawing is about the western blot results on immunity of peripheral blood mononuclear cells (PBMCs).

SPECIFIC EMBODIMENTS AND FORMULAS

Here below, this invention will be described in detail through embodiments without imposing any adverse constraints upon this invention.

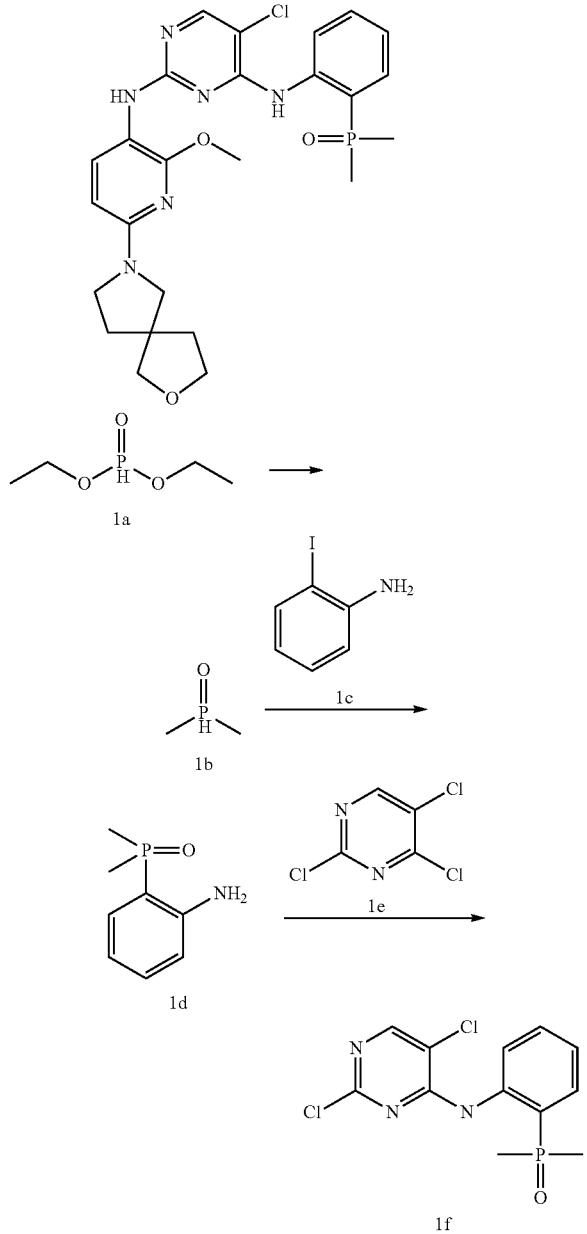

Embodiment 1

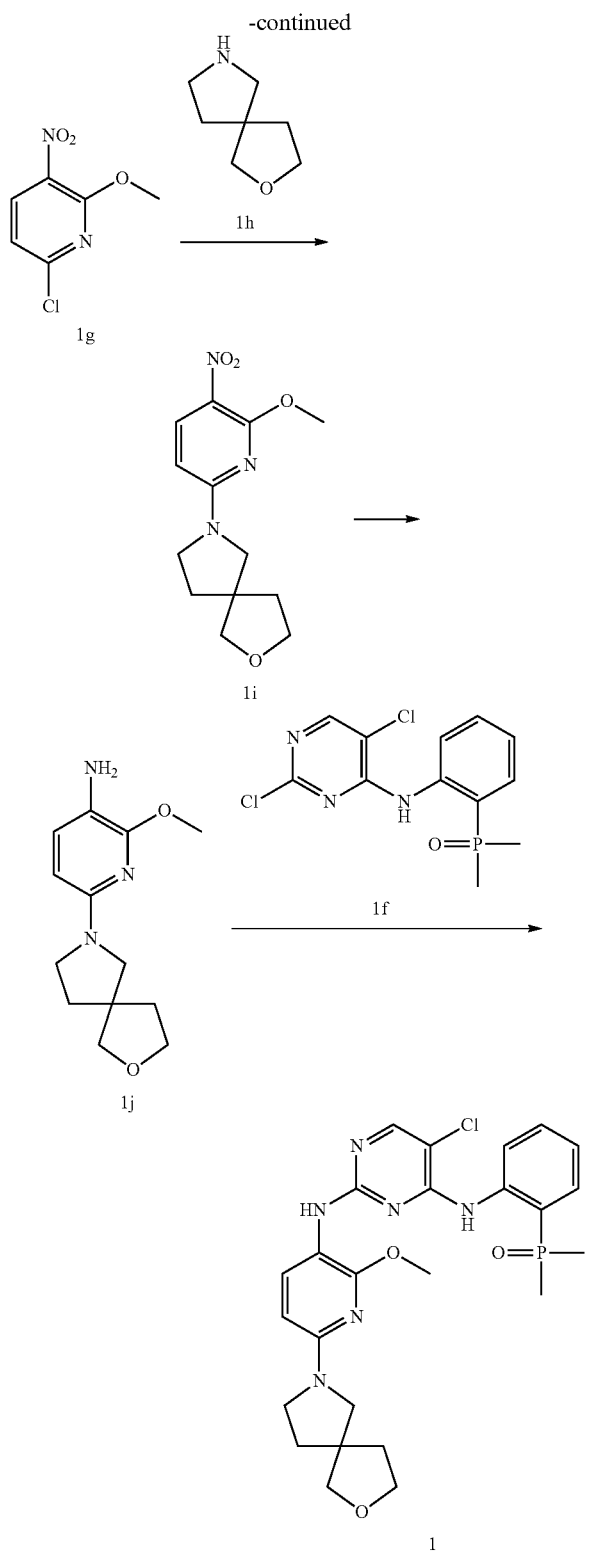

mL saturated sodium bicarbonate solution and 160 mL ethanol to the reaction liquid in succession. Much solid thereby precipitates. Filter the white solid away; concentrate the filtrate to 40 mL and add 150 mL methylbenzene. After concentration, add 130 mL dichloromethane and 13 mL ethanol. Stir them for 1 hour and filter them. Directly use the filtrate in the next step 1b after it is concentrated crude.

$^1$H NMR: (400 MHz, CDCl$_3$) δ 1.59 (dd, J=3.6, 14.4 Hz, 6H).

Step 2

Put 1c (12.50 g, 57.07 mmol), 1b (5.35 g, 68.49 mmol), tripotassium orthophosphate (14.54 g, 68.49 mmol), 9,9-Dimethyl-4,5-bis(diphenylphosphino)xanthene (660.44 mg, 1.14 mmol) and palladium acetate (256.26 mg, 1.14 mmol) in N,N-dimethylformamide (1N, 80 mL). Protected by nitrogen, the reaction mixture is heated to 150° C. and stirred for 16 hours. Filter and concentrate the mixture. Dilute the obtained residues with aqueous hydrochloric acid solution (1N, 80 mL). Regulate the pH value to be about 2 and filter the obtained mixture. Next, extract the filtrate with dichloromethane (100 mL×2) to separate the aqueous layer. Use sodium bicarbonate solution to regulate the pH value to be approximately 9, and then, extract the solution with dichloromethane (200 mL×2). Dry up the organic layer with anhydrous sodium sulfate and concentrate the organic layer until it becomes dry. Purify the crude products through recrystallization (petroleum ether:ethyl acetate=5:1) and get 1d. $^1$H NMR: (400 MHz, CDCl$_3$) δ 7.20 (m, 1H), 7.04 (m, 1H), 6.69-6.58 (m, 2H), 5.35 (br, s, 2H), 1.75 (s, 3H), 1.71 (s, 3H).

Calculated value of MS-ESI: [M+H]+ 170. The actual value is 170.1.

Step 3

At 16° C., add ethyldiisopropylamine (3.82 g, 29.6 mmol) to the N,N-dimethylformamide (20 mL) mixture of 1d (2.50 g, 14.8 mmol) and 1e (2.85 g, 15.5 mmol). Then, heat the reaction mixture to 70° C. and stir it for 16 hours. Dilute the reaction mixture with water (50 mL) and extract it with ethyl acetate (40 mL×3). Rinse the combined organic phase with saturated brine (20 mL×2). Dry up the organic phase with anhydrous sodium sulfate, filter it and concentrate it with vacuum. The crude product is recrystallized in ethanol, and 1f is thereby obtained. $^1$H NMR: (400 MHz, CD$_3$OD) δ 8.50 (m, 1H), 8.35-8.28 (m, 1H), 7.69-7.59 (m, 2H), 7.36-7.28 (m, 1H), 1.91 (s, 3H), 1.88 (s, 3H).

Calculated value of MS-ESI is [M+H]$^+$ 316; 317; 318, and the actual value is 316; 317; 318.

Step 4

Add potassium carbonate (73.3 mg, 530 µmol) to N,N-dimethylformamide (1.00 mL) solution of 1g (50.0 mg, 265 µmol) and 1h (43.4 mg, 265 µmol) as reaction liquid at 50° C. and stir it for 16 hours. Steam the reaction liquid dry; separate and purify the crude product using preparative thin layer chromatography to obtain 1i. The calculated value of MS-ESI is [M+H]$^+$ 280, and the actual value is 280.

Step 5

Add palladium carbon (5.00 mg, 10%) to the ethyl acetate (3.00 mL) solution of 1i (60.0 mg, 215 µmol), and stir it for 8 hours at 20° C. and under hydrogen (50 psi) conditions.

Slowly add 1a (20.00 g, 144.82 mmol, 18.69 mL) to tetrahydrofuran solution (300 mL) of methylmagnesium bromide (3.0 M tetrahydrofuran solution, 160.00 mL, 480 mmol) drop by drop at 0° C., and keep the internal temperature below 10° C. Stir the solution for 5 hours after the temperature slowly rises to room temperature. At the end of reaction, place the reaction liquid in ice bath. Then, add 40

Filter and steam the reaction liquid dry to obtain 1j. The calculated value of MS-ESI is [M+H]$^+$ 250, and the actual value is 250.

Step 6

Add methanesulfonato (2-di-t-butylphosphino-2',4',6'-triisopropyl-1,1-biphenyl) (2'-amino-1,1-biphenyl-2-yl) palladium (II) (7.97 mg, 10.0 μmol) to the tetrahydrofuran (4.00 mL) solution of 1j (50.0 mg, 200 μmol), 1f (63.4 mg, 200 μmol) and sodium tert-butoxide (38.6 mg, 401 μmol). Stir the reaction liquid for 16 hours at 65° C. Filter and steam the reaction liquid dry. Separate and purify the crude product with high performance liquid chromatography to obtain 1.

$^1$H NMR (400 MHz, CD$_3$OD) δ 8.39-8.30 (br s, 1H), 8.10-7.91 (m, 1H), 7.72-7.52 (m, 2H), 7.49-7.38 (m, 1H), 7.26-7.15 (m, 1H), 5.91 (d, J=8.4 Hz, 1H), 3.97 (t, J=7.2 Hz, 2H), 3.90 (s, 3H), 3.77-3.67 (m, 2H), 3.62-3.43 (m, 4H), 2.15-1.97 (m, 4H), 1.87 (s, 3H), 1.84 (s, 3H). The calculated value of MS-ESI is [M+H]$^+$ 529 and 531, while the actual value is 529 and 531.

Embodiment 2

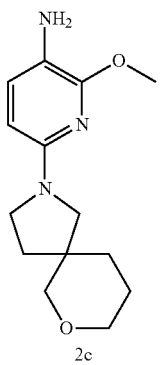

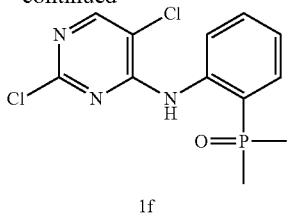

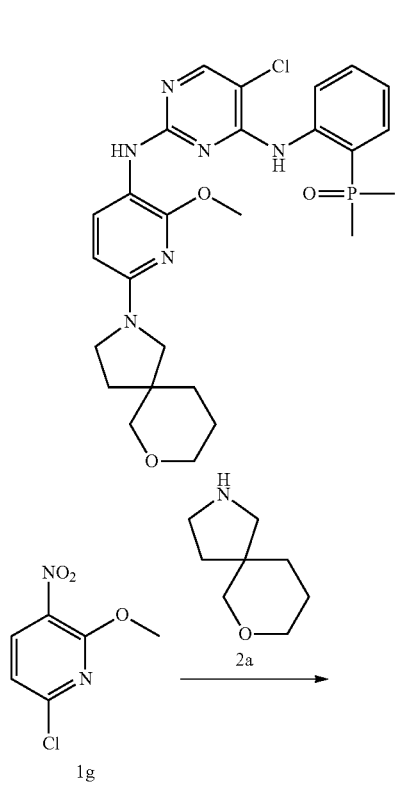

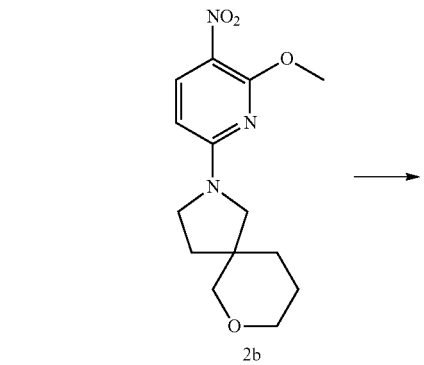

Step 1

Follow Step 1 of Embodiment 1 to obtain 2b. The calculated value of MS-ESI is [M+H]$^+$ 294, and the actual value is 294.

Step 2

Follow Step 2 of Embodiment 1 to obtain 2c. The calculated value of MS-ESI is [M+H]$^+$ 264, and the actual value is 264.

Step 3

Follow Step 3 of Embodiment 1 to obtain 2. $^1$H NMR (400 MHz, CD$_3$°D) δ 8.35 (br s, 1H), 8.00 (s, 1H), 7.66-7.53 (m, 2H), 7.46-7.38 (m, 1H), 7.24-7.18 (m, 1H), 5.91 (d, J=8.4 Hz, 1H), 3.91 (s, 3H), 3.80-3.73 (m, 1H), 3.70-3.63 (m, 1H), 3.61-3.45 (m, 5H), 3.26-3.20 (m, 1H), 2.11-1.96 (m, 2H), 1.87 (s, 3H), 1.84 (s, 3H), 1.82-1.68 (m, 4H). The calculated value of MS-ESI is [M+H]$^+$ 543 and 545, while the actual value is 543 and 545

Embodiment 3

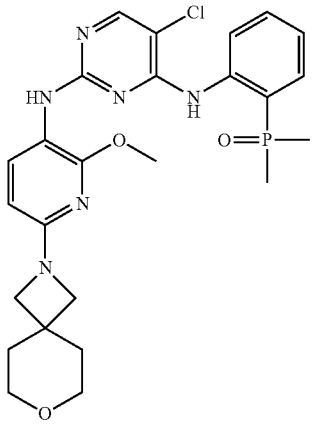

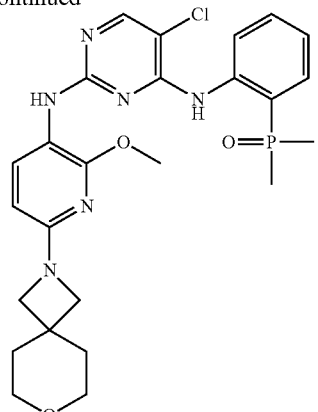

3

Step 1

Follow Step 1 of Embodiment 1 to obtain 3b. The calculated value of MS-ESI is [M+H]$^+$ 280, and the actual value is 280.

Step 2

Follow Step 2 of Embodiment 1 to obtain 3c. The calculated value of MS-ESI is [M+H]$^+$ 250, and the actual value is 250.

Step 3

Follow Step 3 of Embodiment 1 to obtain 3. NMR (400 MHz, CD$_3$OD) δ 8.33 (br s, 1H), 8.02 (s, 1H), 7.72 (d, J=8.4 Hz, 1H), 7.63-7.56 (m, 1H), 7.53-7.44 (m, 1H), 7.28-7.20 (m, 1H), 5.89 (d, J=8.4 Hz, 1H), 3.91 (s, 3H), 3.78 (s, 4H), 20 3.74-3.67 (m, 4H), 1.91-1.79 (m, 10H). The calculated value of MS-ESI is [M+H]$^+$ 529 and 531, while the actual value is 529 and 531.

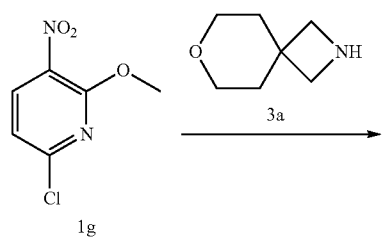

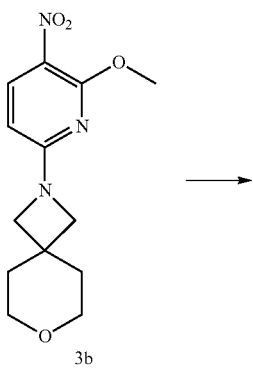

Embodiment 4

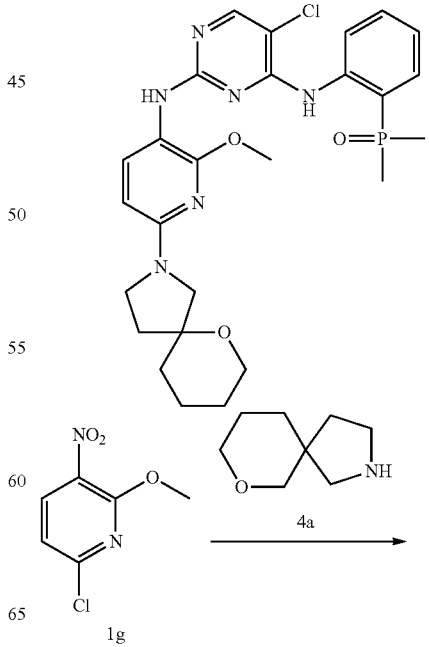

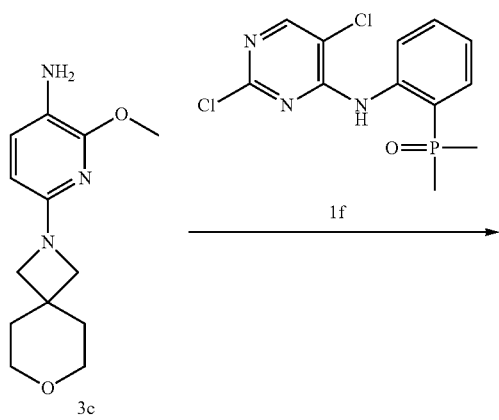

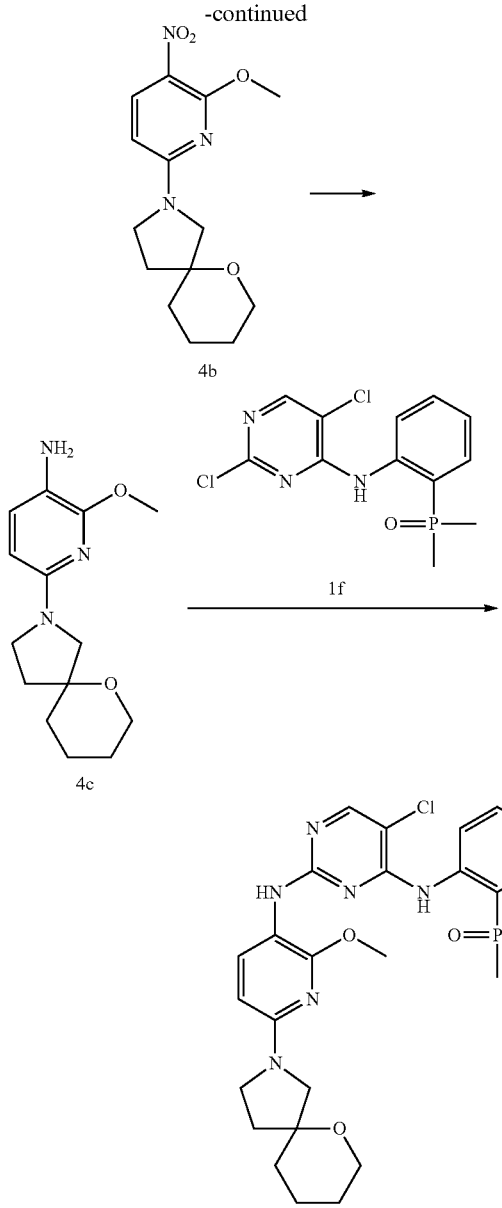

3.83-3.67 (m, 3H), 3.60-3.46 (m, 2H), 3.41-3.35 (m, 1H), 2.39-2.27 (m, 1H), 2.00-1.89 (m, 1H), 1.87 (s, 3H), 1.83 (s, 3H), 1.80-1.68 (m, 4H), 1.66-1.55 (m, 2H). The calculated value of MS-ESI is [M+H]⁺ 543 and 545, while the actual value is 543 and 545.

Embodiment 5

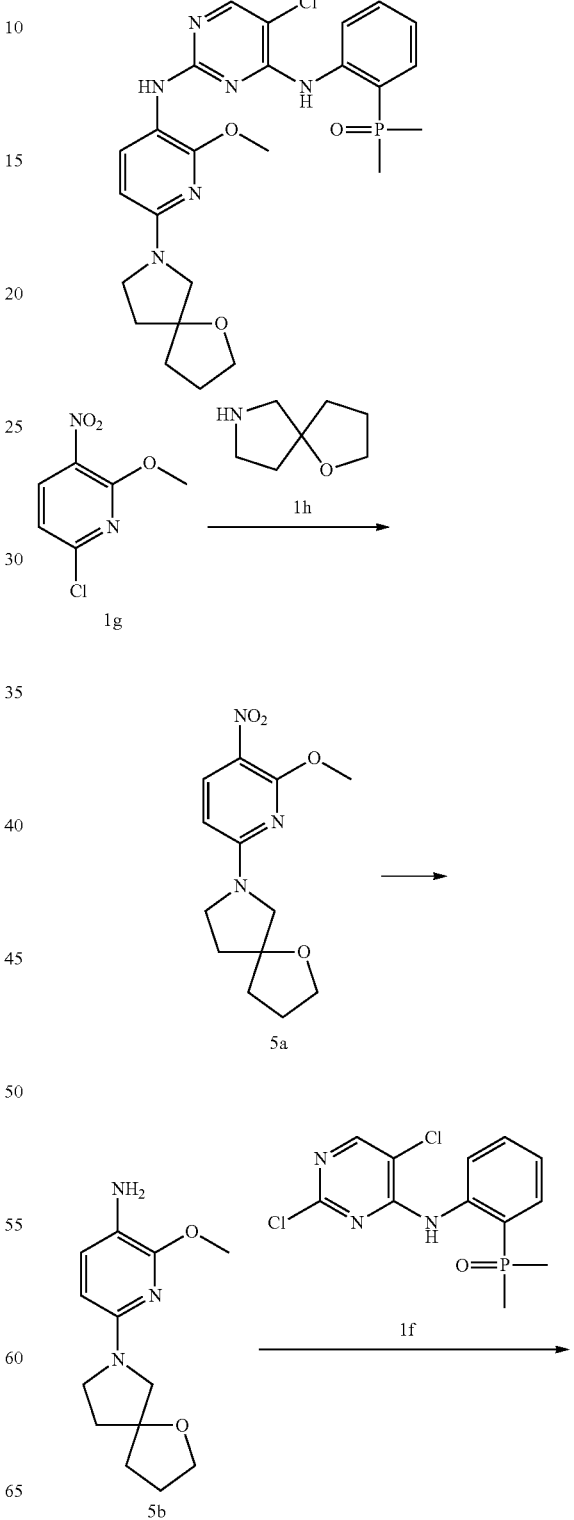

Step 1

Follow Step 1 of Embodiment 1 to obtain 4b. The calculated value of MS-ESI is [M+H]⁺ 294, and the actual value is 294.

Step 2

Follow Step 2 of Embodiment 1 to obtain 4c. The calculated value of MS-ESI is [M+H]⁺ 264, and the actual value is 264.

Step 3

Follow Step 3 of Embodiment 1 to obtain 4. ¹H NMR (400 MHz, CD₃OD) δ 8.34 (br s, 1H), 7.99 (s, 1H), 7.62 (d, J=8.4 Hz, 1H), 7.59-7.51 (m, 1H), 7.45-7.37 (m, 1H), 7.23-7.12 (m, 1H), 5.89 (d, J=8.4 Hz, 1H), 3.90 (s, 3H),

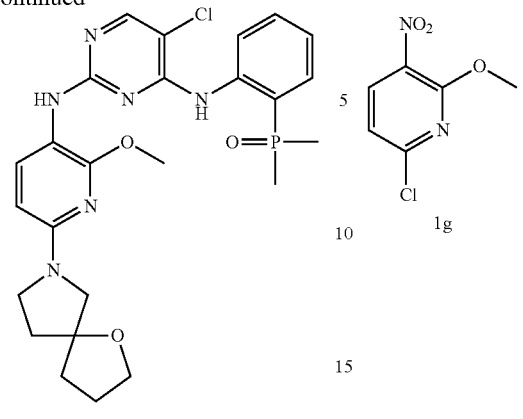

5

Step 1

Follow Step 1 of Embodiment 1 to obtain 5a. The calculated value of MS-ESI is [M+H]$^+$ 280, and the actual value is 280.

Step 2

Follow Step 2 of Embodiment 1 to obtain 5b. The calculated value of MS-ESI is [M+H]$^+$ 250, and the actual value is 250.

Step 3

Follow Step 3 of Embodiment 1 to obtain 5. $^1$H NMR (400 MHz, CD$_3$OD) δ 8.31 (br s, 1H), 8.02 (s, 1H), 7.72 (d, J=8.0 Hz, 1H), 7.64-7.54 (m, 1H), 7.52-7.44 (m, 1H), 7.28-7.20 (m, 1H), 5.91 (d, J=8.4 Hz, 1H), 3.93-3.87 (m, 5H), 3.86-3.81 (m, 2H), 3.75-3.69 (m, 2H), 1.91-1.82 (m, 8H), 1.79-1.71 (m, 2H), 1.63-1.55 (m, 2H). The calculated value of MS-ESI is [M+H]$^+$ 529 and 531, while the actual value is 529 and 531.

Embodiment 6

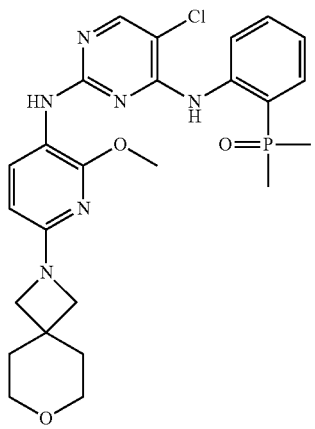

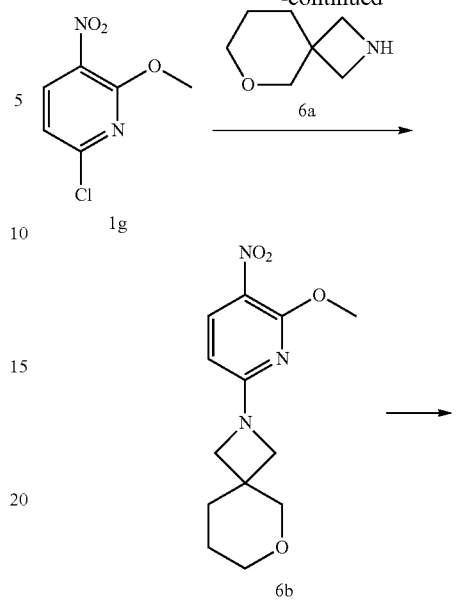

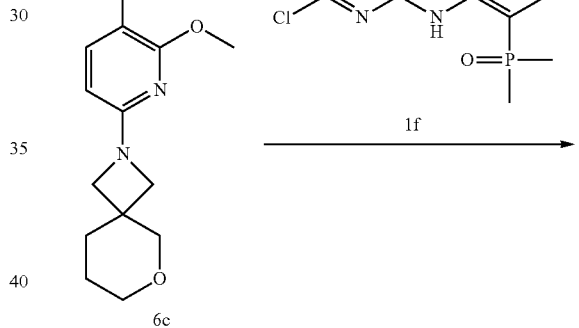

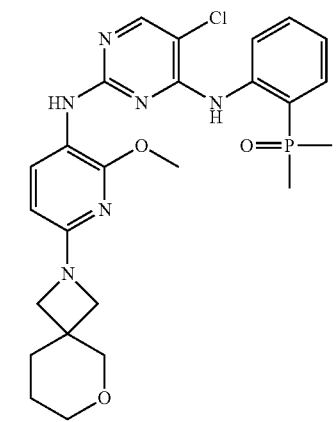

Step 1

Follow Step 1 of Embodiment 1 to obtain 6b. The calculated value of MS-ESI is [M+H]$^+$ 280, and the actual value is 280.

Step 2

Follow Step 2 of Embodiment 1 to obtain 6c. The calculated value of MS-ESI is [M+H]$^+$ 250, and the actual value is 250.

Step 3

Follow Step 3 of Embodiment 1 to obtain 6. $^1$H NMR (400 MHz, CD$_3$OD) δ 8.33 (br s, 1H), 8.02 (s, 1H), 7.72 (d, J=8.0 Hz, 1H), 7.64-7.55 (m, 1H), 7.51-7.45 (m, 1H), 7.27-7.22 (m, 1H), 5.88 (d, J=8.4 Hz, 1H), 3.90 (s, 3H), 3.78-3.73 (m, 4H), 3.69-3.63 (m, 4H), 1.94-1.89 (m, 2H), 1.87 (s, 3H), 1.84 (s, 3H), 1.70-1.63 (m, 2H). The calculated value of MS-ESI is [M+H]$^+$ 529 and 531, while the actual value is 529 and 531.

Embodiment 7

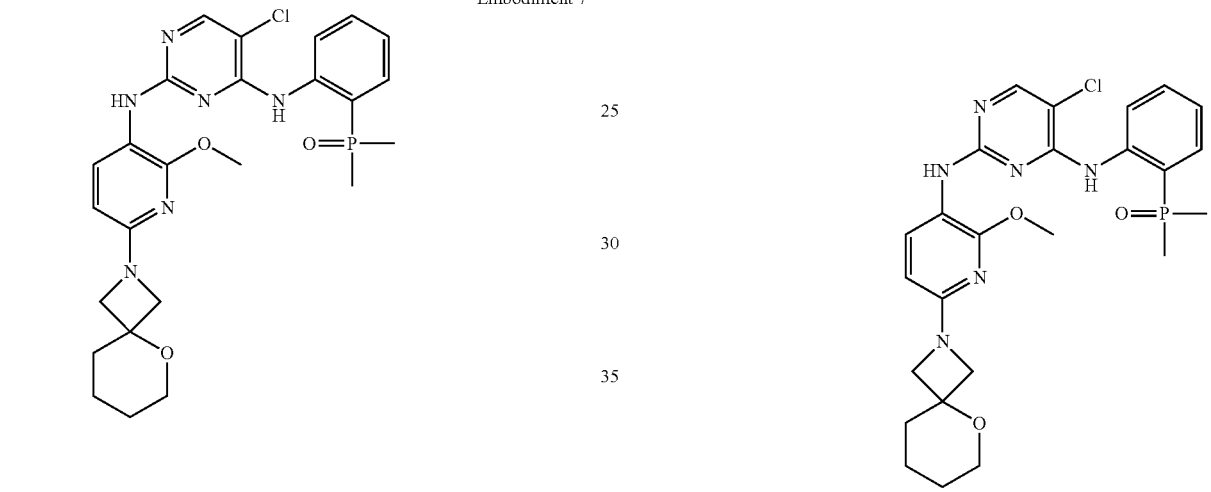

7

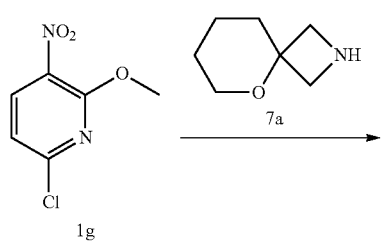

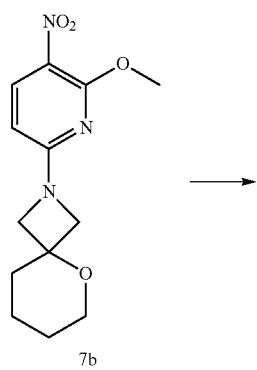

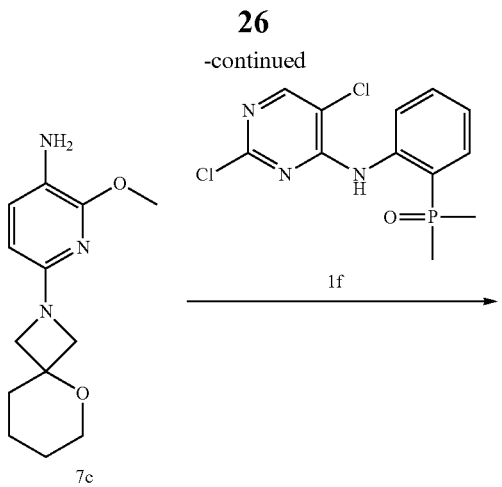

Step 1

Follow Step 1 of Embodiment 1 to obtain 7b. The calculated value of MS-ESI is [M+H]$^+$ 280, and the actual value is 280.

Step 2

Follow Step 2 of Embodiment 1 to obtain 7c. The calculated value of MS-ESI is [M+H]$^+$ 250, and the actual value is 250.

Step 3

Follow Step 3 of Embodiment 1 to obtain 7. $^1$H NMR (400 MHz, CD$_3$OD) δ 8.34 (br s, 1H), 7.99 (s, 1H), 7.69-7.50 (m, 2H), 7.42 (br s, 1H), 7.24-7.14 (m, 1H), 5.89 (br d, J=8.4 Hz, 1H), 3.90 (s, 5H), 3.67-3.39 (m, 4H), 2.29-1.95 (m, 6H), 1.87 (s, 3H), 1.84 (s, 3H). The calculated value of MS-ESI is [M+H]$^+$ 529 and 531, while the actual value is 529 and 531.

Embodiment 8

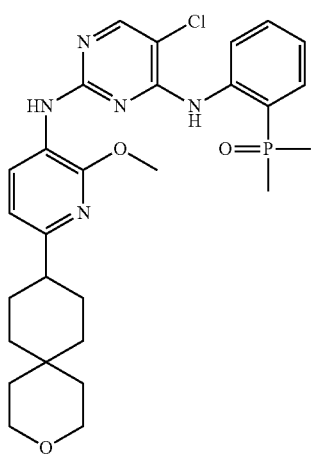

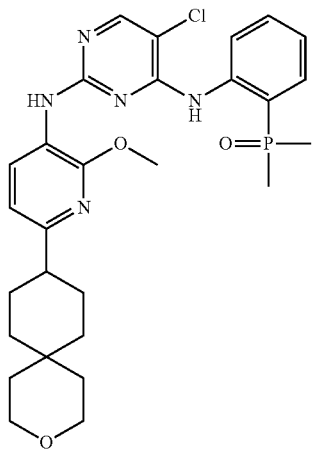

8

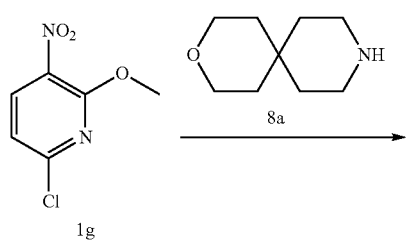

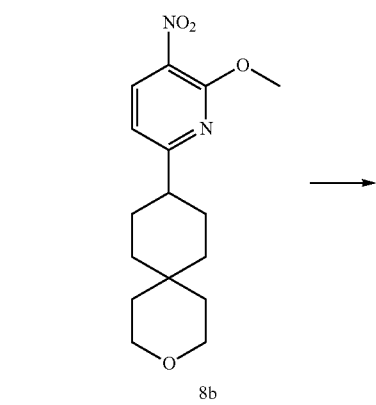

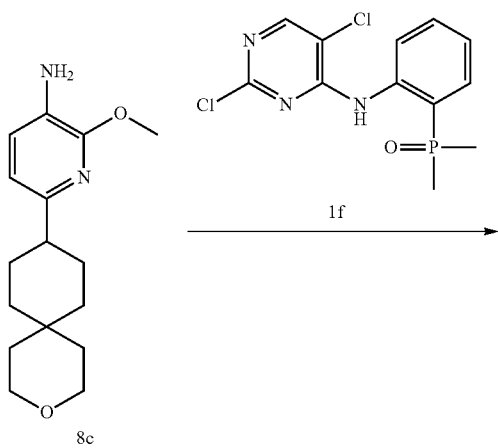

Step 1

Follow Step 1 of Embodiment 1 to obtain 8b. The calculated value of MS-ESI is [M+H]$^+$ 308, and the actual value is 308.

Step 2

Follow Step 2 of Embodiment 1 to obtain 8c. The calculated value of MS-ESI is [M+H]$^+$ 278, and the actual value is 278.

Step 3

Follow Step 3 of Embodiment 1 to obtain 8. $^1$H NMR (400 MHz, 44) δ 8.41-8.28 m, 1H), 8.01 (s, 1H), 7.75 (d, J=8.4 Hz, 1H), 7.64-7.53 (m, 1H), 7.47 (t, J=8.0 Hz, 1H), 7.27-7.19 (m, 1H), 6.20 (d, J=8.4 Hz, 1H), 3.89 (s, 3H), 3.79-3.67 (m, 4H), 3.58-3.44 (m, 4H), 1.87 (s, 3H), 1.83 (s, 3H), 1.71-1.63 (m, 4H), 1.62-1.54 (m, 4H). The calculated value of MS-ESI is [M+H]$^+$557 and 559, while the actual value is 557 and 559.

Embodiment 9

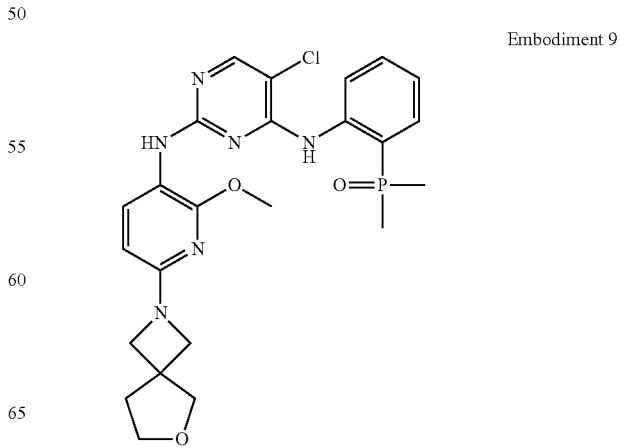

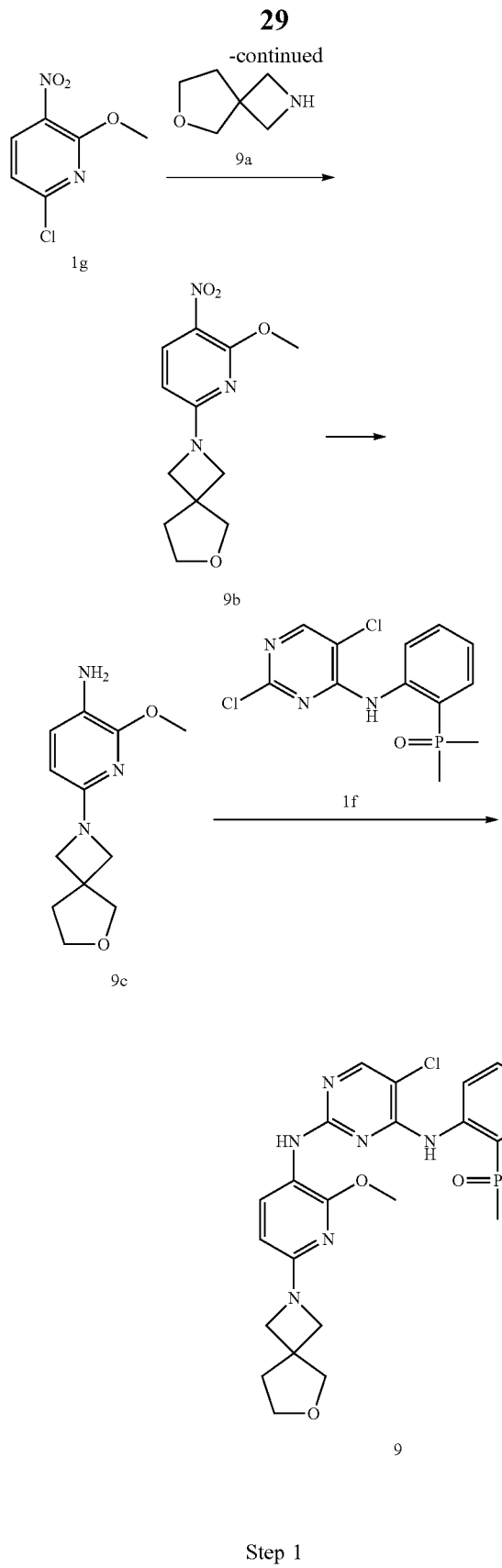

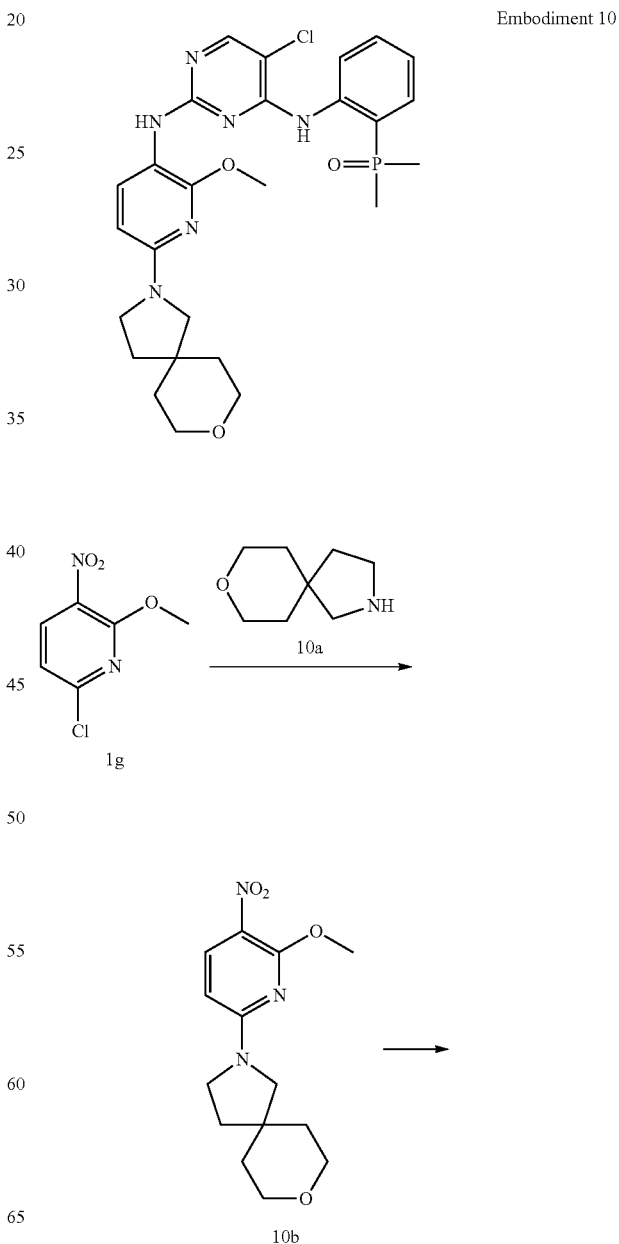

Step 2

Follow Step 2 of Embodiment 1 to obtain 9c. The calculated value of MS-ESI is [M+H]$^+$ 236, and the actual value is 236.

Step 3

Follow Step 3 of Embodiment 1 to obtain 9. $^1$H NMR (400 MHz, CD$_3$OD) δ 8.21 (br s, 1H), 7.91 (s, 1H), 7.65 (d, J=8.4 Hz, 1H), 7.53-7.44 (m, 1H), 7.42-7.32 (m, 1H), 7.18-7.09 (m, 1H), 5.79 (d, J=8.4 Hz, 1H), 3.89-3.74 (m, 11H), 2.13 (t, J=7.2 Hz, 2H), 1.76 (s, 3H), 1.73 (s, 3H). The calculated value of MS-ESI is [M+H]+ 515 and 517, while the actual value is 515 and 517.

Embodiment 10

Step 1

Follow Step 1 of Embodiment 1 to obtain 9b. The calculated value of MS-ESI is [M+H]$^+$ 266, and the actual value is 266.

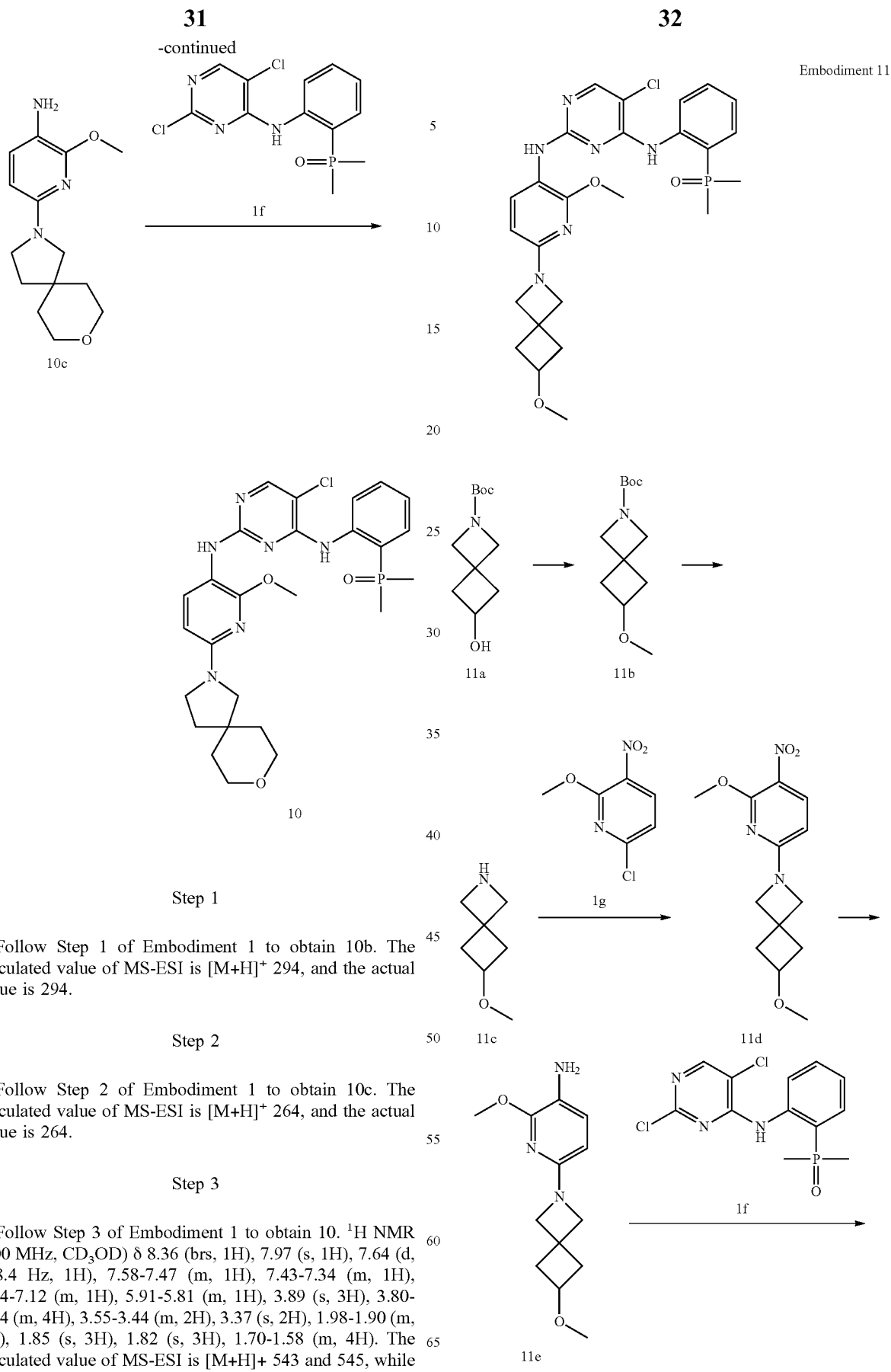

Step 1

Follow Step 1 of Embodiment 1 to obtain 10b. The calculated value of MS-ESI is [M+H]+ 294, and the actual value is 294.

Step 2

Follow Step 2 of Embodiment 1 to obtain 10c. The calculated value of MS-ESI is [M+H]+ 264, and the actual value is 264.

Step 3

Follow Step 3 of Embodiment 1 to obtain 10. $^1$H NMR (400 MHz, CD$_3$OD) δ 8.36 (brs, 1H), 7.97 (s, 1H), 7.64 (d, J=8.4 Hz, 1H), 7.58-7.47 (m, 1H), 7.43-7.34 (m, 1H), 7.24-7.12 (m, 1H), 5.91-5.81 (m, 1H), 3.89 (s, 3H), 3.80-3.64 (m, 4H), 3.55-3.44 (m, 2H), 3.37 (s, 2H), 1.98-1.90 (m, 2H), 1.85 (s, 3H), 1.82 (s, 3H), 1.70-1.58 (m, 4H). The calculated value of MS-ESI is [M+H]+ 543 and 545, while the actual value is 543 and 545.

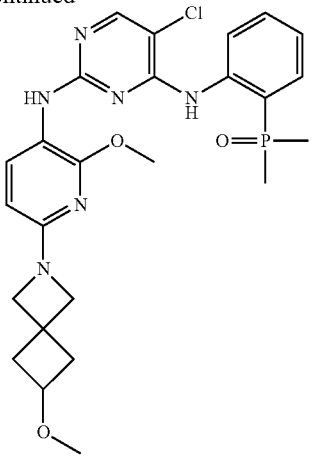

11

Dissolve 11a (320 mg, 1.50 mmol) in tetrahydrofuran (8.0 mL). Add sodium hydride (480 mg, 12.0 mmol, 60% purity) at 0° C. and stir the mixture for 10 minutes. Then, add iodomethane (1.70 g, 12.0 mmol) and stir the mixture for 2 hours at room temperature. Add water for quenching and extract with ethyl acetate. Combine the organic phase and dry it with anhydrous sodium sulfate. Filter and concentrate it with vacuum. The residues are separated and purified with preparative thin layer chromatography to obtain 11b.

$^1$H NMR (400 MHz, CDCl$_3$) δ 3.89 (s, 2H), 3.86 (s, 2H), 3.77-3.73 (m, 1H), 3.21 (s, 3H), 2.47-2.44 (m, 2H), 2.09-2.04 (m, 2H), 1.42 (s, 9H).

Step 2

Dissolve 11b (300 mg, 1.32 mmol) in dichloromethane (6.0 mL), and then, add trifluoroacetic acid (1.51 g, 13.2 mmol) at 0° C. The reaction liquid is directly concentrated to obtain 11c.

$^1$H NMR (400 MHz, CDCl$_3$) δ 4.09 (s, 2H), 4.04 (s, 2H), 3.84-3.81 (m, 1H), 3.23 (s, 3H), 2.64-2.59 (m, 2H), 2.19-2.14 (m, 2H).

Step 3

Dissolve 1g (110 mg, 0.583 mmol) and 11c (148 mg, 1.17 mmol) in AW-dimethylformamide (2.0 mL). Then, add potassium carbonate (322 mg, 2.33 mmol), and stir the mixture for 16 hours at 50° C. After complete reaction, cool the reaction down to the room temperature. Add water (2.0 mL) and extract the reaction liquid with ethyl acetate (8.0 mL×3). Combine the organic phase and rinse it with saturated brine (10.0 mL×3). Dry the organic phase up with anhydrous sodium sulfate and filter it. Concentrate filtrate under reduced pressure. Separate and purify the residues with preparative thin-layer chromatography to obtain 11d.

$^1$H NMR (400 MHz, CDCl$_3$) δ 8.24 (d, J=8.0 Hz, 1H), 5.77 (d, J=9.2 Hz, 1H), 4.15 (s, 2H), 4.12 (s, 2H), 4.03 (s, 3H), 3.89-3.82 (m, 1H), 3.26 (s, 3H), 2.62-2.56 (m, 2H), 2.23-2.18 (m, 2H).

Step 4

Dissolve 11d (74.0 mg, 0.265 mmol) in the ethyl acetate (10.0 mL), and add wet palladium carbon (7.0 mg, 10%). Stir the reaction liquid under hydrogen (50 psi) atmosphere at 25° C. for 8 hours. After complete reaction, filter the reaction liquid and concentrate the filtrate under reduced pressure to obtain 11e.

$^1$H NMR (400 MHz, CDCl$_3$) δ 6.87 (d, J=7.6 Hz, 1H), 5.76 (d, J=8.0 Hz, 1H), 3.92 (s, 3H), 3.88 (s, 2H), 3.84 (s, 2H), 3.82-3.79 (m, 1H), 3.24 (s, 3H), 2.54-2.50 (m, 2H), 2.15-2.10 (m, 2H), 1.60 (s, 2H).

Step 5

Dissolve 1f (85.0 mg, 0.269 mmol), 11e (67.0 mg, 0.269 mmol) and sodium tert-butoxide (51.7 mg, 0.537 mmol) in tetrahydrofuran (2.0 mL). With the protection of nitrogen, add [2-(di-tert-butylphosphino)-2',4',6'-triisopropyl-1,1'-biphenyl](2'-amino-[1,1'-biphenyl]-2-yl) palladium (II) (10.7 mg, 0.0134 mmol) to the reaction liquid, Stir the reaction liquid for 16 hours at 70° C. Filter the reaction liquid and dry it up. Purify it to with preparative high performance liquid chromatography to obtain 11.

$^1$H NMR (400 MHz, CDCl$_3$) δ 10.82 (s, 1H), 8.58 (dd, J=4.0, 8.0 Hz, 1H), 8.16 (d, J=8.4 Hz, 1H), 8.07 (s, 1H), 7.47 (t, J=8.0 Hz, 1H), 7.31-7.28 (m, 1H), 7.14-7.10 (m, 1H), 6/91 (s, 1H), 5.82 (d, J=8.4 Hz, 1H), 3.96 (s, 2H), 3.94 (s, 3H), 3.92 (s, 2H), 3.87-3.80 (m, 1H), 3.25 (s, 3H), 2.57-2.52 (m, 2H), 2.18-2.13 (m, 2H), 1.85 (s, 3H), 1.82 (s, 3H).

The calculated value of MS-ESI is [M+H]$^+$ 529 and 531, while the actual value is 529 and 531.

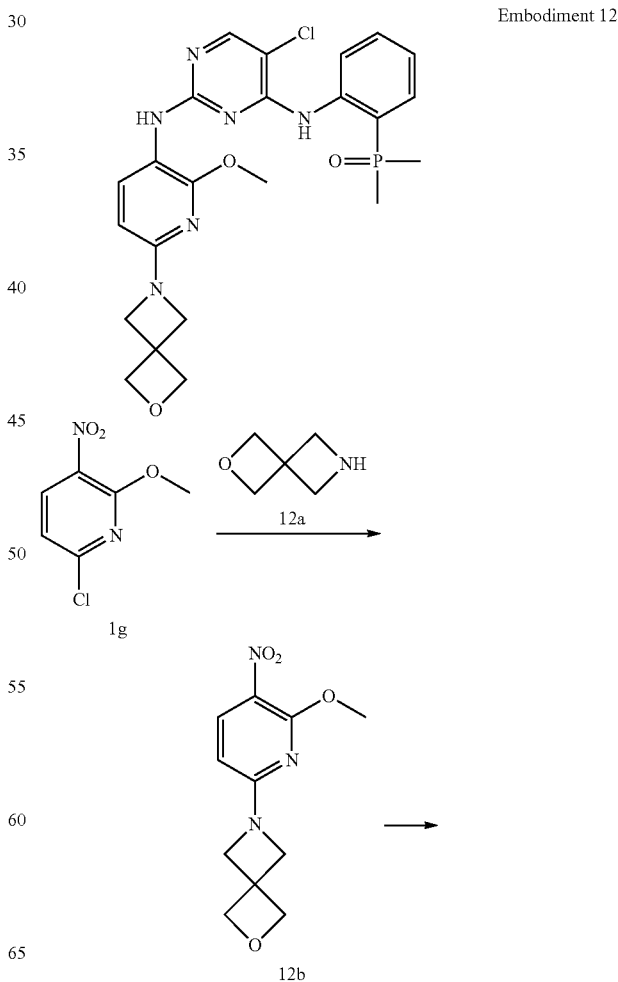

Embodiment 12

-continued

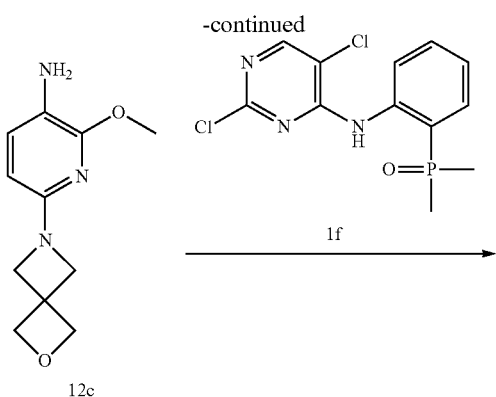

12c

Step 1

Dissolve 1g (200 mg, 1.06 mmol) and 12a (116 mg, 1.17 mmol) in N,N-dimethylformamide (5.0 mL). Then, add potassium carbonate (366 mg, 2.65 mmol) to the reaction liquid and stir it for 4 hours at 25° C. After complete reaction, add water (5 mL) and extract the reaction liquid with dichloromethane (10 mL×3). Combine the organic phase and rinse it with saturated brine (40 mL). Dry it up with anhydrous sodium sulphate and filter it. Concentrate the filtrate under reduced pressure. Add petroleum ether and ethyl acetate at a ratio of 1/1 (20 mL/20 mL) to the residues and stir the mixture for 0.5 hours. Filter it and obtain 12b.

The calculated value of MS-ESI is [M+H]$^+$ 252, and the actual value is 252.

Step 2

Dissolve 12b (250 mg, 0.995 mmol) in ethyl acetate (10.0 mL) and add wet palladium (7.00 mg, 10%) to the solution. The reaction lasts for 8 hours under the hydrogen (50 psi) atmosphere and at 25° C. After complete reaction, filter and concentrate the solution to obtain 12c.

$^1$H NMR (400 MHz, DMSO-d$_6$) δ 6.84 (d, J=8.0 Hz, 1H), 5.77 (d, J=8.0 Hz, 1H), 4.68 (s, 4H), 4.09 (s, 2H), 3.90 (s, 4H), 3.79 (s, 3H).

The calculated value of MS-ESI is [M+H]$^+$ 222, and the actual value is 222.

Step 3

Dissolve 1f (85.0 mg, 0.269 mmol), 12c (59.5 mg, 0.269 mmol) and sodium tert-butoxide (51.7 mg, 0.538 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (10.7 mg, 0.0134 mmol) with the protection of nitrogen, and stir the reaction liquid for 16 hours at 70° C. Filter and steam the reaction liquid dry. Purify it with preparative high performance liquid chromatography to obtain 12.

$^1$H NMR (400 MHz, CDCl$_3$) δ 10.85 (s, 1H), 8.58 (dd, J=4.0, 8.4 Hz, 1H), 8.22 (d, J=8.4 Hz, 1H), 8.07 (s, 1H), 7.48 (t, J=8.0 Hz, 1H), 7.32-7 (m, 1H), 7.15-7.11 (m, 1H), 6.94 (s, 1H), 5.86 (d, J=8.4 Hz, 1H), 4.85 (s, 4H), 4.12 (s, 4H), 3.95 (s, 3H), 1.86 (s, 3H), 1.82 (s, 3H).

The calculated value of MS-ESI is [M+H]$^+$ 501 and 503. while the actual value is 501 and 503.

Embodiment 13

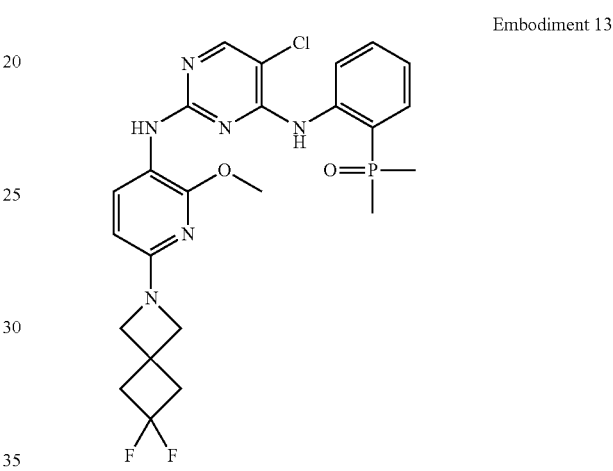

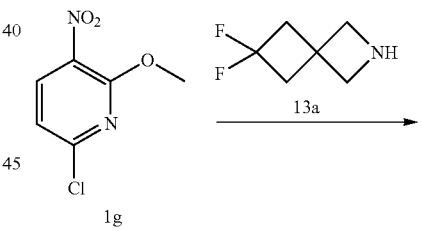

1g

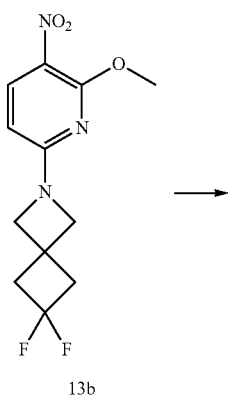

13b

-continued

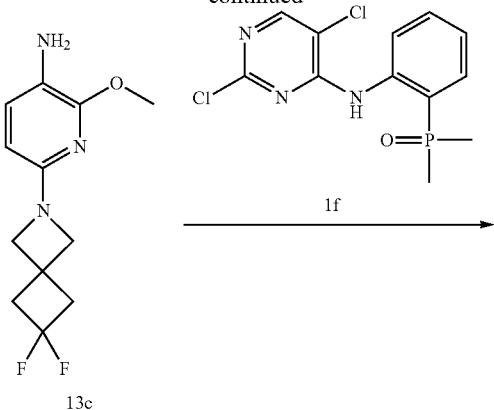

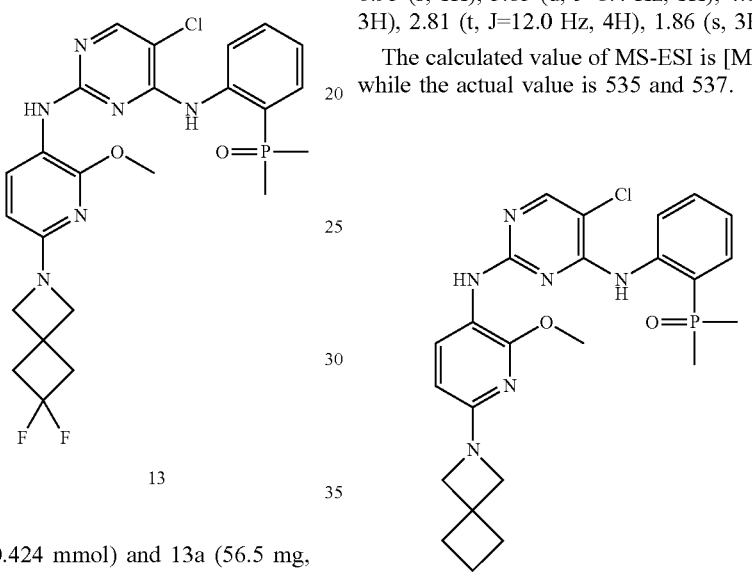

Dissolve 1g (80.0 mg, 0.424 mmol) and 13a (56.5 mg, 0.424 mmol) in A/N-dimethylformamide (5.0 mL). Then, add potassium carbonate (147 mg, 1.06 mmol) to the reaction liquid and stir it for 16 hours at 50° C. After complete reaction, add water (5 mL) and extract the reaction liquid with dichloromethane (10 mL×3). Combine the organic phase and rinse it with saturated brine (40 mL). Dry it up with anhydrous sodium sulphate and filter it. Concentrate the filtrate under reduced pressure. Add petroleum ether and ethyl acetate at a ratio of 1/1 (20 mL/4 mL) to the residues and stir the mixture for 0.5 hours. Filter it and obtain 13b.

$^1$H NMR (400 MHz, CDCl$_3$) δ 8.26 (d, J=8.8 Hz, 1H), 5.80 (d, J=8.8 Hz, 1H), 4.25 (s, 4H), 4.04 (s, 3H), 2.87 (t, J=12.0 Hz, 4H).

The calculated value of MS-ESI is [M+H]$^+$ 286, and the actual value is 286.

Step 2

Dissolve 13b (75.0 mg, 0.263 mmol) in ethyl acetate (10.0 mL) and add wet palladium (7.00 mg, 10%) to the solution. The reaction lasts for 8 hours under the hydrogen (50 psi) atmosphere and at 25° C. After complete reaction, filter and concentrate the solution to obtain 13c.

$^1$H NMR (400 MHz, CDCl$_3$) δ 6.88 (d, J=8.0, Hz, 1H), 5.79 (d, J=8.0 Hz, 1H), 3.96 (s, 4H), 3.93 (s, 3H), 3.31 (s, 2H), 2.78 (t, J=12.0 Hz, 4H).

The calculated value of MS-ESI is [M+H]+ 256, and the actual value is 256.

Step 3

Dissolve 1f (70.0 mg, 0.221 mmol), 13c (56.5 mg, 0.221 mmol) and sodium tert-butoxide (53.2 mg, 0.553 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (8.8 mg, 0.0111 mmol) with the protection of nitrogen, and stir the reaction liquid for 16 hours at 70° C. Filter and steam the reaction liquid dry. Purify it with preparative high performance liquid chromatography to obtain 13.

$^1$H NMR (400 MHz, CDCl$_3$) δ 10.83 (s, 1H), 8.58 (dd, J=4.4, 8.4 Hz, 1H), 8.22 (d, J=8.4 Hz, 1H), 8.07 (s, 1H), 7.48 (t, J=8.0 Hz, 1H), 7.31-7.28 (m, 1H), 7.15-7.10 (m, 1H), 6.95 (s, 1H), 5.85 (d, J=8.4 Hz, 1H), 4.04 (s, 4H), 3.94 (s, 3H), 2.81 (t, J=12.0 Hz, 4H), 1.86 (s, 3H), 1.82 (s, 3H).

The calculated value of MS-ESI is [M+H]$^+$ 535 and 537, while the actual value is 535 and 537.

Embodiment 14

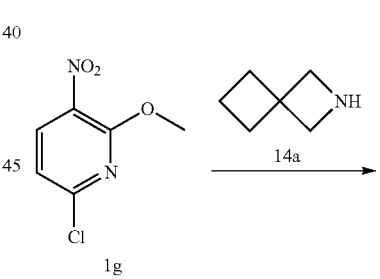

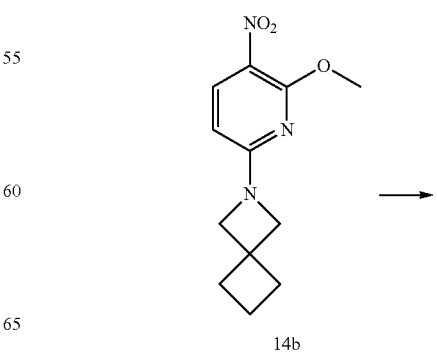

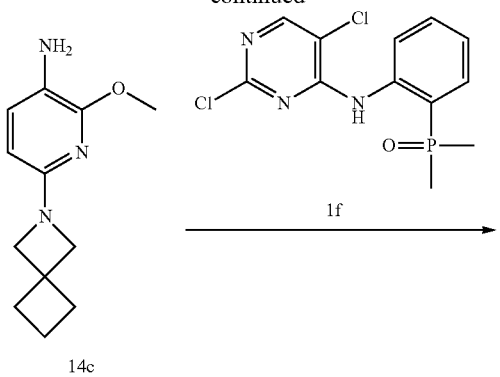

Step 1

Dissolve 1g (100 mg, 0.530 mmol) and 14a (51.5 mg, 0.530 mmol) in N,N-dimethylformamide (5.0 mL). Then, add potassium carbonate (183 mg, 1.33 mmol) to the reaction liquid and stir it for 16 hours at 50° C. After complete reaction, add water (5 mL) and extract the reaction liquid with dichloromethane (10 mL×3). Combine the organic phase and rinse it with saturated brine (40 mL). Dry it up with anhydrous sodium sulphate and filter it. Concentrate the filtrate under reduced pressure. Add petroleum ether (20 mL) to the residues and stir the mixture for 0.5 hours. Filter it and obtain 14b.

$^1$H NMR (400 MHz, CDCl$_3$) δ 8.23 (d, J=9.2 Hz, 1H), 5.76 (d, J=9.2 Hz, 1H), 4.11 (s, 4H), 4.03 (s, 3H), 2.26 (t, J=7.6 Hz, 4H), 1.95-1.87 (m, 2H).

Step 2

Dissolve 14b (50.0 mg, 0.201 mmol) in ethyl acetate (10.0 mL) and add wet palladium (7.00 mg, 10%) to the solution. Let the reaction last for 8 hours under the hydrogen (50 psi) atmosphere and at 25° C. After complete reaction, filter and concentrate the solution to obtain 14c.

$^1$H NMR (400 MHz, CDCl$_3$) δ 6.87 (d, J=8.0 Hz, 1H), 5.76 (d, J=8.0, Hz, 1H), 3.93 (s, 3H), 3.84 (s, 4H), 3.26 (s, 2H), 2.19 (t, J=7.6 Hz, 4H), 1.90-1.82 (m, 2H).

Step 3

Dissolve 1f (57.0 mg, 0.180 mmol), 14c (39.5 mg, 0.180 mmol) and sodium tert-butoxide (43.3 mg, 0.451 mmol) in tetrahydrofuran (2.0 mL). Add (2-di-tert-butylphosphino-2', 4',6'-triisopropyl-1,1'-biphenyl) (2'-amino-1,1-biphenyl-2-yl) palladium (II) (7.2 mg, 0.009 mmol) with the protection of nitrogen, and stir the reaction liquid for 16 hours at 70° C. Filter and steam the reaction liquid dry. Purify it with preparative high performance liquid chromatography to obtain 14.

$^1$H NMR (400 MHz, CDCl$_3$) δ 10.81 (s, 1H), 8.58 (dd, J=4.4, 8.2 Hz, 1H), 8.12 (d, J=8.4 HZ, 1H), 8.06 (s, 1H), 7.47 (t, J=7.6 Hz, 1H), 7.30-7.24 (m, 1H), 7.13-7.09 (m, 1H), 6.91 (s, 1H), 5.82 (d, J=8.4 Hz, 1H), 3.93 (s, 3H), 3.92 (s, 4H), 2.21 (t, J=7.6 Hz, 4H), 1.91-1.88 (m, 2H), 1.85 (s, 3H), 1.81 (s, 3H).

The calculated value of ES-ESI is [M+H]$^+$ 499 and 501, while the actual value is 499 and 501.

Embodiment 15

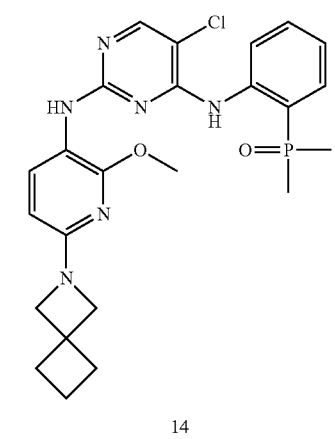

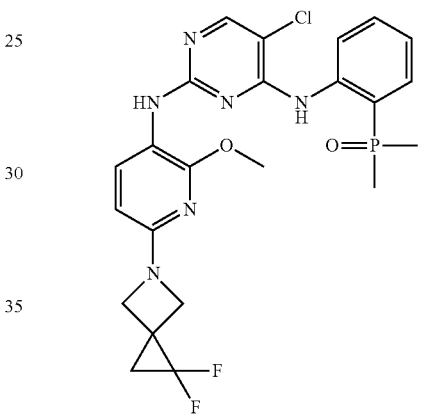

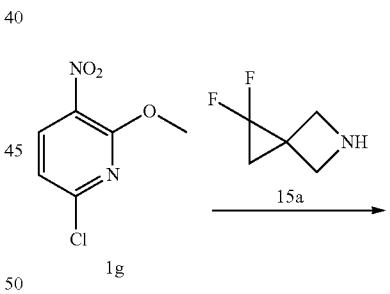

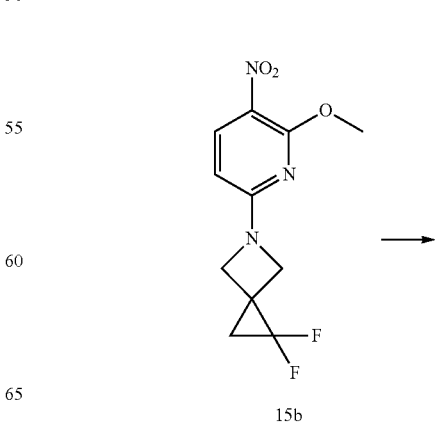

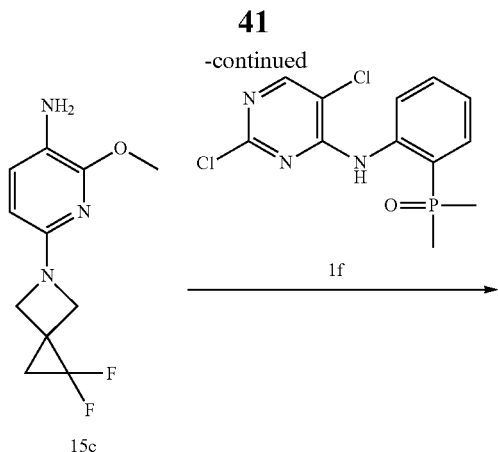

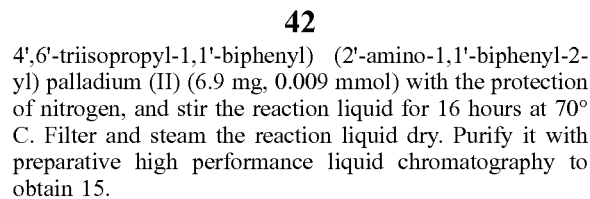

4',6'-triisopropyl-1,1'-biphenyl) (2'-amino-1,1'-biphenyl-2-yl) palladium (II) (6.9 mg, 0.009 mmol) with the protection of nitrogen, and stir the reaction liquid for 16 hours at 70° C. Filter and steam the reaction liquid dry. Purify it with preparative high performance liquid chromatography to obtain 15.

$^1$H NMR (400 MHz, CDCl$_3$) δ 10.84 (s, 1H), 8.58 (dd, J=4.4, 8.4 Hz, 1H), 8.24 (d, J=8.4 Hz, 1H), 8.08 (s, 1H), 7.48 (t, J=7.6 Hz, 1H), 7.32-7.26 (m, 1H), 7.12 (t, J=7.6 Hz, 1H), 6.97 (s, 1H), 5.90 (d, J=8.4 Hz, 1H), 4.21 (d, J=8.4 Hz, 2H), 4.04 (d, J=8.4 Hz, 2H), 3.95 (s, 3H), 1.86 (s, 3H), 1.83 (s, 3H), 1.50 (t, J=8.4 Hz, 2H).

The calculated value of MS-ESI is [M+H]$^+$ 521 and 523; the actual value is 521 and 523.

Embodiment 16

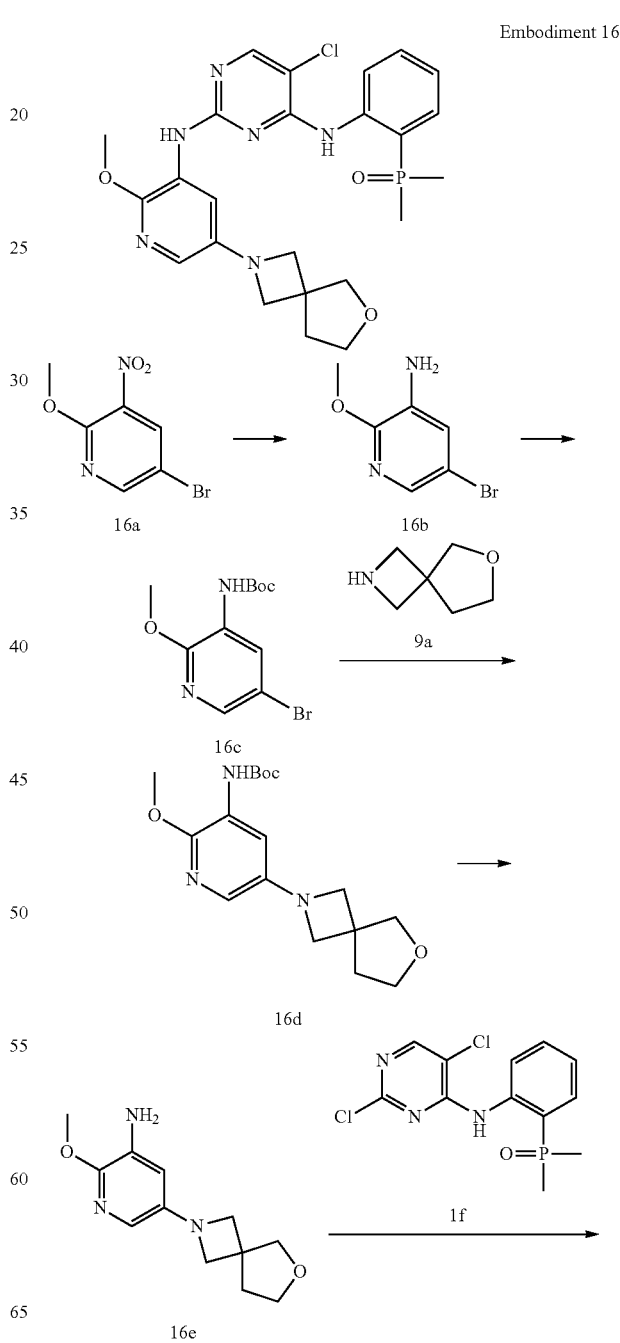

Dissolve 1g (100 mg, 0.530 mmol) and 15a (1 mg, 0.530 mmol) in N,N-dimethylformamide (5.0 mL). Then, add potassium carbonate (183 mg, 1.33 mmol) to the reaction liquid and stir it for 16 hours at 50° C. After complete reaction, add water (5 mL) and extract the reaction liquid with dichloromethane (10 mL×3). Combine the organic phase and rinse it with saturated brine (40 mL). Dry it up with anhydrous sodium sulphate and filter it. Concentrate the filtrate under reduced pressure. Add petroleum ether and ethyl acetate (20 mL/20 mL) to the residues and stir the mixture for 2 hours. Filter it and obtain 15b.

$^1$H NMR (400 MHz, CDCl$_3$) δ 8.29 (d, J=8.8 Hz, 1H), 5.86 (d, J=8.8 Hz, 1H), 4.38 (d, J=9.2 Hz, 2H), 4.22 (d, J=9.2 Hz, 2H), 4.05 (s, 3H), 1.60 (t, J=8.4 Hz, 2H).

Step 2

Dissolve 15b (100 mg, 0.369 mmol) in ethyl acetate (10.0 mL) and add wet palladium (7.00 mg, 10%) to the solution. Let the reaction last for 8 hours under the hydrogen (50 psi) atmosphere and at 25° C. After complete reaction, filter and concentrate the solution. Separate and purify the residues with chromatography column to obtain 15c.

$^1$H NMR (400 MHz, CDCl$_3$) δ 6.91 (d, J=7.6 Hz, 1H), 5.83 (d, J=7.6 Hz, 1H), 4.14 (d, J=8.0 Hz, 2H), 3.96 (d, J=8.0 Hz, 2H), 3.94 (s, 3H), 3.33 (s, 2H), 1.46 (t, J=8.4 Hz, 2H).

Step 3

Dissolve 1f (55.0 mg, 0.174 mmol), 15c (42.0 mg, 0.174 mmol) and sodium tert-butoxide (41.8 mg, 0.435 mmol) in tetrahydrofuran (2.0 mL). Add (2-di-tert-butylphosphino-2',

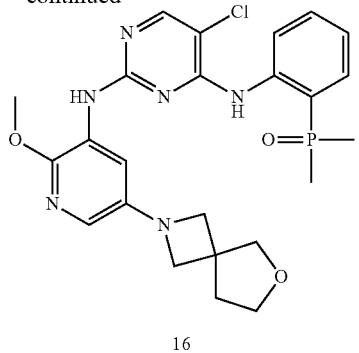

16

Step 1

Dissolve 16a (300 mg, 1.29 mmol) and ammonium chloride (345 mg, 6.45 mmol) in ethanol (6.0 mL) and water (2.0 mL). Add iron dust (720 mg, 12.9 mmol) to the reaction liquid and stir the mixture for 6 hours at 25° C. At the end of the reaction, filter and concentrate the mixture. Extract the filtrate with ethyl acetate (5 mL×3) and separate the aqueous layer. Dry up the organic layer with anhydrous sodium sulphate and concentrate it until it becomes dry to obtain 16b.

$^1$H NMR (400 MHz, DMSO-d$_6$) δ7.38 (d, J=2.4 Hz, 1H), 6.98 (d, J=2.4 Hz, 1H), 5.29 (s, 2H), 3.83 (s, 3H).

Step 2

Dissolve 16b (255 mg, 1.26 mmol) and triethylamine (152 mg, 1.51 mmol) in dichloromethane (5 mL). Add the mixture of di-tert-butyl dicarbonate (329 mg, 1.51 mmol) and 4-dimethylaminopyridine (154 mg, 1.26 mmol) dissolved in dichloromethane. Stir for 16 hours at 50° C. At the end of reaction, add water (10 mL) and extract the reaction liquid with dichloromethane (10 mL×3). Combine the organic phase, dry it with anhydrous sodium sulphate and filter it. Concentrate the filtrate under reduced pressure. Separate and purify the residues with chromatography column to obtain 16c.

$^1$H NMR (400 MHz, CDCl$_3$) δ 8.48 (s, 1H), 7.82 (d, J=2.4 Hz, 1H), 6.95 (s, 1H), 3.98 (s, 3H), 1.54 (s, 9H)

Step 3

Dissolve 16c (90.0 mg, 0.297 mmol), 9a (33.6 mg, 0.297 mmol) and sodium tert-butoxide (71.3 mg, 0.742 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (11.8 mg, 0.0148 mmol) with the protection of nitrogen, and stir the reaction liquid for 16 hours at 70° C. Filter and steam the reaction liquid dry. Isolate and purify the residues with preparation thin-layer chromatography to obtain 16d.

$^1$H NMR (400 MHz, CDCl$_3$) δ 7.66 (s, 1H), 7.02 (d, J=2.4 Hz, 1H), 6.97 (s, 1H), 3.93 (s, 3H), 3.92 (s, 2H), 3.87-3.84 (m, 6H), 1.53 (s, 9H).

The calculated value of MS-ESI is [M+H]$^+$ 336, and the actual value is 336.

Step 4

Dissolve 16d (75.0 mg, 0.224 mmol) in dichloromethane (3.0 mL). Add trifluoroacetic acid (1.00 mL) to the reaction liquid at 0° C., and stir the reaction liquid for 4 hours at 25° C. Directly concentrate the reaction liquid to obtain 16e.

$^1$H NMR (400 MHz, CDCl$_3$) δ 7.02 (d, J=2.4 Hz, 1H), 6.64 (d, J=2.4 Hz, 1H), 4.19 (s, 3H), 4.08 (s, 4H), 3.98 (s, 2H), 3.93 (t, J=7.2 Hz, 2H), 2.28 (t, J=7.2 Hz, 2H).

Step 5

Dissolve 1f (70.0 mg, 0.221 mmol), 16e (52.0 mg, 0.221 mmol) and sodium tert-butoxide (85.1 mg, 0.886 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (8.8 mg, 0.0111 mmol) with the protection of nitrogen and stir the reaction liquid for 16 hours at 70° C. Filter and steam the reaction liquid dry. Purify it with preparative high performance liquid chromatography to obtain 16.

$^1$H NMR (400 MHz, CDCl$_3$) δ 10.95 (s, 1H), 8.59 (dd, J=4.4, 8.4 Hz, 1H), 8.17 (s, 1H), 7.99 (d, J=2.4 Hz, 1H), 7.60 (t, J=8.0 Hz, 1H), 7.44 (s, 1H), 7.35-7.29 (m, 1H), 7.17-7.13 (m, 1H), 7.03 (d, J=2.8 Hz, 1H), 3.99 (s, 3H), 3.90 (s, 2H), 3.85 (t, J=8.0 Hz, 2H), 3.69 (s, 4H), 2.17 (t, J=8.0 Hz, 2H), 1.89 (s, 3H), 1.86 (s, 3H).

The calculated value of MS-ESI is [M+H]$^+$ 515 and 517; the actual value is 515 and 517.

Embodiment 17

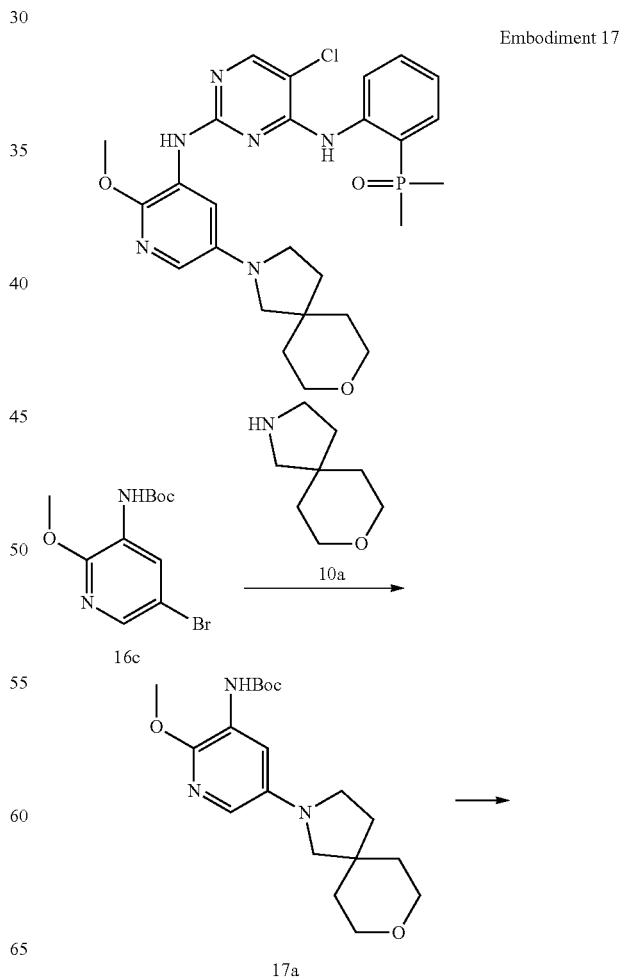

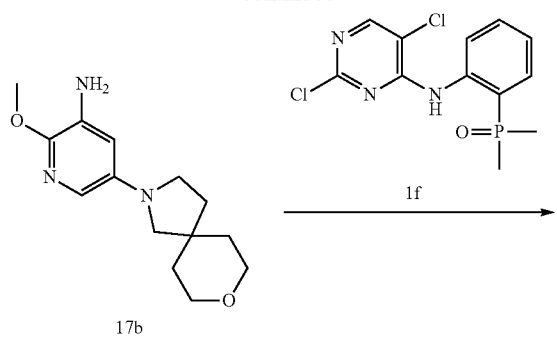

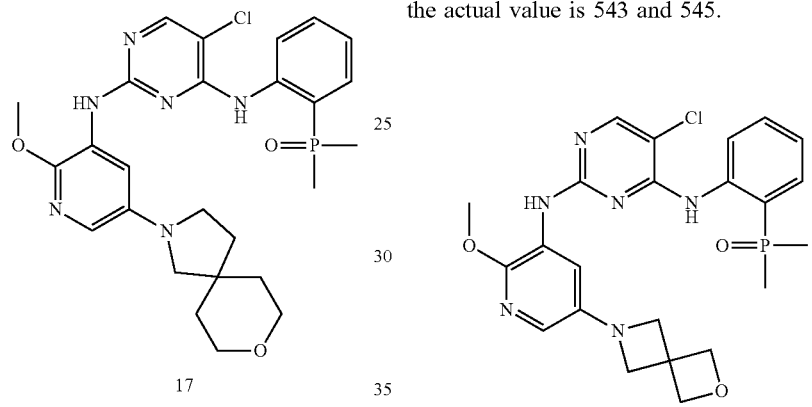

Step 1

Dissolve 16c (100 mg, 0.330 mmol), 10a (46.6 mg, 0.297 mmol) and sodium tert-butoxide (79.3 mg, 0.825 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (13.1 mg, 0.0165 mmol) with the protection of nitrogen, and stir the reaction liquid for 16 hours at 70° C. Add water (1.0 mL) to the reaction liquid and extract the reaction liquid with ethyl acetate (5.0 mL×3). Dry up the organic phase with anhydrous sodium sulphate. Filter and spin the organic phase dry. Separate and purify the residues with preparative thin-layer chromatography to obtain 17a.

$^1$H NMR: (400 MHz, CDCl$_3$) δ 7.77 (s, 1H), 7.08 (d, J=2.8 Hz, 1H), 6.97 (s, 1H), 3.93 (s, 3H), 3.76-3.66 (m, 4H), 3.35 (t, 7 10=6.8 Hz, 2H), 3.18 (s, 2H), 1.92 (t, J=6.8 Hz, 2H), 1.68-1.60 (m, 4H), 1.54 (s, 9H).

Step 2

Dissolve 17a (45.0 mg, 0.124 mmol) in dichloromethane (3.00 mL). Add trifluoroacetic acid (1.0 mL) to the reaction liquid at 0° C., and stir the reaction liquid for 4 hours at 25° C. Directly concentrate the reaction liquid to obtain 17b.

The calculated value of MS-ESI is [M+H]$^+$ 264, and the actual value is 264.

Step 3

Dissolve 17b (32.0 mg, 0.120 mmol), 1f (38.0 mg, 0.120 mmol) and sodium tert-butoxide (46.2 mg, 0.480 mmol in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (4.8 mg, 0.006 mmol) with the protection of nitrogen, and stir the reaction liquid for 16 hours at 100° C. Filter and steam the reaction liquid dry. Purify it with preparative high performance liquid chromatography to obtain 17.

$^1$H NMR (400 MHz, CDCl$_3$) δ 10.94 (s, 1H), 8.62 (dd, J=4.4, 8.4 Hz, 1H), 8.18 (s, 1H), 8.07 (d, J=2.4 Hz, 1H), 7.51 (t, J=8.0 Hz, 1H), 7.38 (s, 1H), 7.33-7.28 (m, 1H), 7.15-7.07 (m, 2H), 3.97 (s, 3H), 3.76-3.68 (m, 2H), 3.67-3.59 (m, 2H), 3.22 (t, J=6.8 Hz, 2H), 3.05 (s, 2H), 1.88 (s, 3H), 1.86 (s, 2H), 1.84 (s, 3H), 1.63-1.59 (m, 4H)

The calculated value of MS-ESI is [M+H]$^+$ 543 and 545; the actual value is 543 and 545.

Embodiment 18

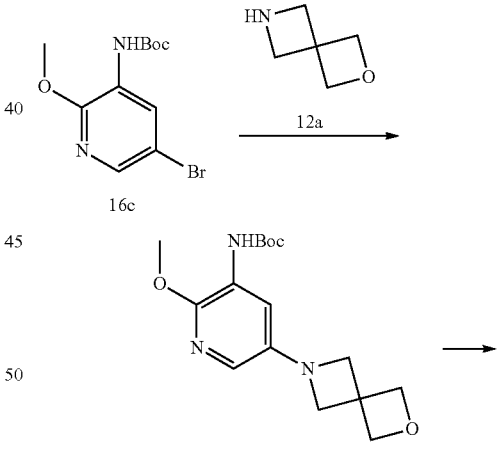

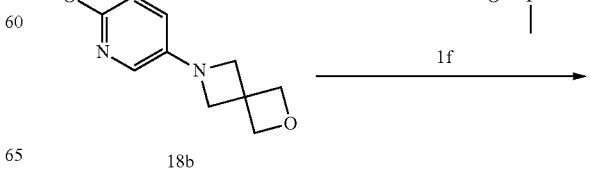

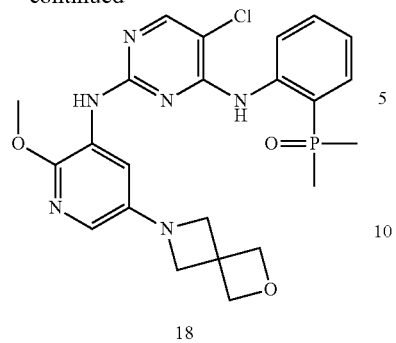

18

Dissolve 18a (100 mg, 0.330 mmol), 12a (32.7 mg, 0.297 mmol) and sodium tert-butoxide (79.3 mg, 0.825 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (13.1 mg, 0.0165 mmol) with the protection of nitrogen, and stir the reaction liquid for 16 hours at 70° C. Add water (3.0 mL) to the reaction liquid and extract the reaction liquid with ethyl acetate (8.0 mL×3). Dry up the organic phase with anhydrous sodium sulphate. Filter and spin the organic phase dry. Separate and purify the residues with preparative thin-layer chromatography to obtain 18a.

$^1$H NMR (400 MHz, CDCl$_3$) δ 7.64 (S, 1H), 7.00 (d, J=2.8 Hz, 1H), 6.97 (s, 1H), 4.83 (s, 4H), 4.00 (s, 4H), 3.93 (s, 3H), 1.53 (s, 9H)

The calculated value of MS-ESI is [M+H]$^+$ 322, and the actual value is 322.

Step 2

Dissolve 18a (70.0 mg, 0.218 mmol) in dichloromethane (3.0 mL). Add trifluoroacetic acid (1.0 mL) to the reaction liquid at 0° C., and stir the reaction liquid for 4 hours at 25° C. Directly concentrate the reaction liquid to obtain 18b.

The calculated value of MS-ESI is [M+H]$^+$ 222, and the actual value is 222.

Step 3

Dissolve 18b (48.0 mg, 0.218 mmol), 1f (69.0 mg, 0.218 mmol) and sodium tert-butoxide (83.9 mg, 0.873 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (8.70 mg, 0.0109 mmol) with the protection of nitrogen, and stir the reaction liquid for 16 hours at 100° C. Filter and steam the reaction liquid dry. Purify it with preparative high performance liquid chromatography to obtain 18.

$^1$H NMR (400 MHz, CDCl$_3$) δ 10.97 (S, 1H), 8.57 (dd, J=4.4, 8.4 Hz, 1H), 8.16 (s, 1H), 7.98 (d, J=2.4 Hz, 1H), 7.57 (t, J=7.6 Hz, 1H), 7.42 (S, 1H), 7.36-7.30 (m, 1H), 7.17-7.12 (m, 1H), 6.99 (d, J=2.4 Hz, 1H), 4.80 (S, 4H), 3.97 (s, 3H), 3.83 (s, 4H), 1.89 (s, 3H), 1.86 (s, 3H)

The calculated value of MS-ESI is [M+H]$^+$ 501 and 503; the actual value is 501 and 503.

Embodiment 19

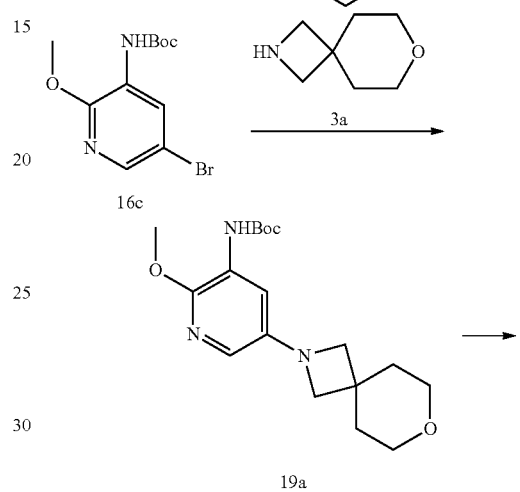

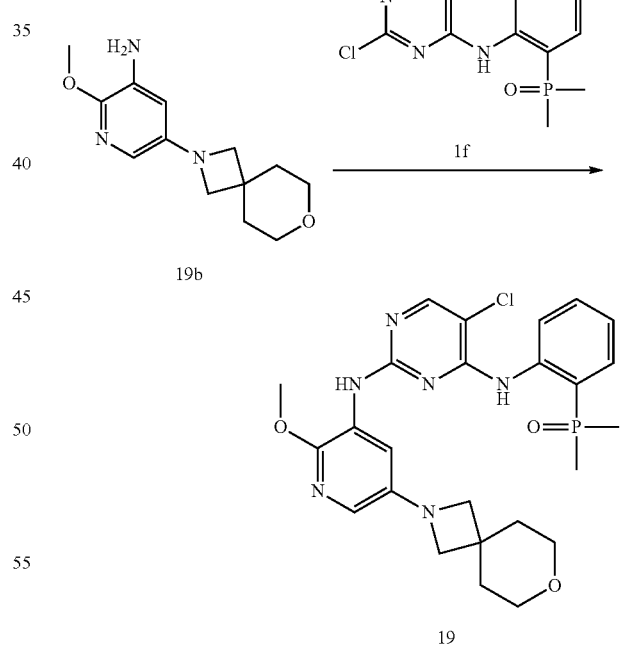

Step 1

Dissolve 16c (100 mg, 0.330 mmol), 3a (42.0 mg, 0.330 mmol) and sodium tert-butoxide (79.3 mg, 0.825 mmol) in tetrahydrofuran (2.0 mL). Add (2-di-tert-butylphosphino-2', 4',6'-triisopropyl-1,1'-biphenyl) (2'-amino-1,1'-biphenyl-2- yl) palladium (II) (13.1 mg, 0.0165 mmol) with the protection of nitrogen, and stir the reaction liquid for 16 hours at 70° C. Add water (3.0 mL) to the reaction liquid and extract the reaction liquid with ethyl acetate (8.0 mL×3). Dry up the organic phase with anhydrous sodium sulphate. Filter and spin the organic phase dry. Separate and purify the residues with preparative thin-layer chromatography to obtain 19a.

Step 2

Dissolve 19a (40.0 mg, 0.114 mmol) in dichloromethane (3.0 mL). Add trifluoroacetic acid (1.0 mL) to the reaction liquid at 0° C., and stir the reaction liquid for 3 hours at 25° C. Directly concentrate the reaction liquid to obtain 19b.

The calculated value of MS-ESI is [M+H]+ 250, and the actual value is 250.

Step 3

Dissolve 1f (35.0 mg, 0.111 mmol), 19b (27.6 mg, 0.111 mmol) and sodium tert-butoxide (42.6 mg, 0.443 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (4.4 mg, 0.006 mmol) with the protection of nitrogen, and stir the reaction liquid for 16 h at 100° C. Filter and steam the reaction liquid dry. Purify it with preparative high performance liquid chromatography to obtain 19.

$^1$H NMR (400 MHz, CDCl$_3$) δ 10.95 (a, 1H), 8.58 (dd, J=4.4, 8.4 Hz, 1H), 8.42 (d, J=2.4 Hz, 1H), 8.18 (s, 1H), 7.54 (t, J=7.6 Hz, 1H), 7.39-7.37 (m, 2H), 7.34-7.29 (m, 1H), 7.16-7.12 (m, 1H), 4.45 (s, 4H), 3.99 (s, 3H), 2.93-2.90 (m, 4H), 1.96-1.93 (m, 4H), 1.88 (S, 3H), 1.85 (S, 3H)

Embodiment 20

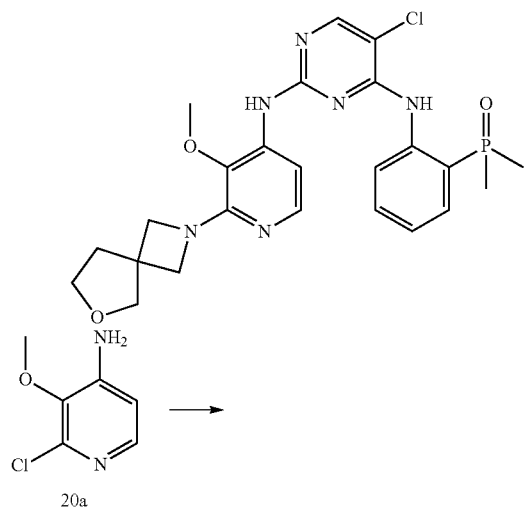

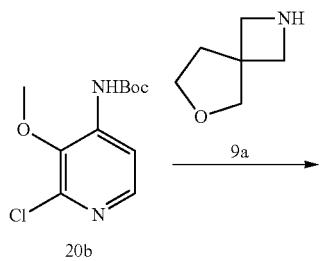

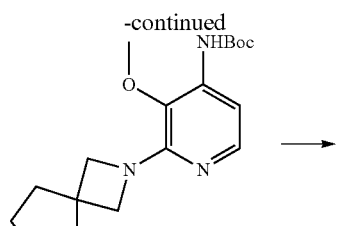

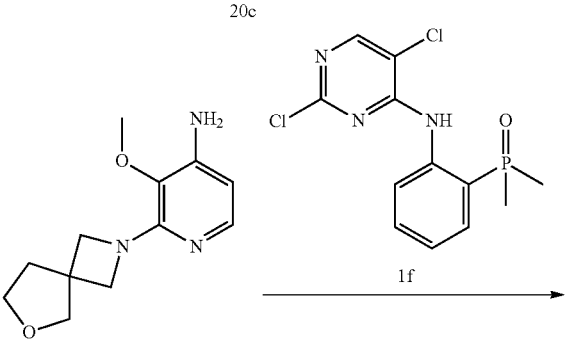

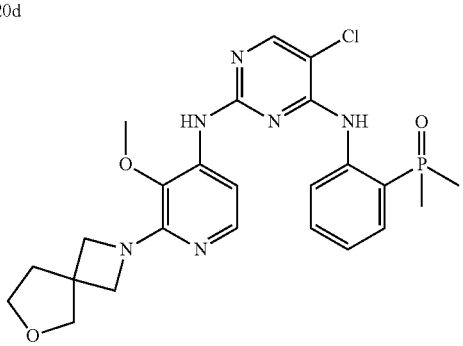

Step 1

Dissolve 20a (1.24 g, 7.82 mmol) and triethylamine (949 mg, 9.38 mmol) in dichloromethane (10.0 mL). Add the dichloromethane solution (10.0 mL) of di-tert-butyl dicarbonate (2.05 g, 9.38 mmol) and 4-dimethylaminopyridine (955 mg, 7.82 mmol) drop by drop. Stir the reaction liquid for 16 hours at 50° C. At the end of reaction, add water (20 mL) and extract the reaction liquid with dichloromethane (20.0 mL×3). Combine the organic phase, dry it with anhydrous sodium sulphate and filter it. Concentrate the filtrate under reduced pressure. Separate and purify the residues with chromatography column to obtain 20b.

The calculated value of MS-ESI is [M+H]+ 259 and 261, and the actual value is 259 and 261.

Step 2

Dissolve 20b (120.0 mg, 0.464 mmol), 9a (52.5 mg, 0.464 mmol), 1,1'-binaphthyl-2,2'-diphenyl phosphine (28.9 mg, 0.046 mmol) and sodium tert-butoxide (111 mg, 1.16 mmol) in 1,4-dioxane (2.00 mL). Add palladium acetate (5.2 mg, 0.023 mmol) to the reaction liquid with the protection of nitrogen, and stir the reaction liquid for 16 hours at 110° C. Add water (1 mL) and extract the reaction liquid with ethyl acetate (5 mL×3). Combine the organic phase, dry it with anhydrous sodium sulphate and filter it. Concentrate the filtrate under reduced pressure. Separate and purify the residues with preparation thin-layer chromatography to obtain 20c.

The calculated value of MS-ESI is [M+H]$^+$ 336, and the actual value is 336.

Step 3

Dissolve 20c (60.0 mg, 0.179 mmol) in dichloromethane (3.0 mL). Add trifluoroacetic acid (1.0 mL) to the reaction liquid at 0° C., and stir the reaction liquid for 3 hours at 25° C. Directly concentrate the reaction liquid to obtain 20d.

The calculated value of MS-ESI is [M+H]$^+$ 236, and the actual value is 236.

Step 4

Dissolve 1f (55.0 mg, 0.174 mmol), 20d (40.9 mg, 0.174 mmol) and sodium tert-butoxide (66.9 mg, 0.696 mmol) in tetrahydrofuran (2.0 mL). Add (2-di-tert-butylphosphino-2',4',6'-triisopropyl-1,1'-biphenyl) (2'-amino-1,1'-biphenyl-2-yl) palladium (II) (6.9 mg, 0.0087 mmol) with the protection of nitrogen, and stir the reaction liquid for 16 hours at 100° C. Filter and steam the reaction liquid dry. Purify it with preparative high performance liquid chromatography to obtain 20.

$^1$H NMR (400 MHz, CDCl$_3$) δ 10.99 (s, 1H), 8.56 (dd, J=4.4, 8.0 Hz, 1H), 8.17 (s, 1H), 7.86-7.85 (m, 1H), 7.81-7.80 (m, 1H), 7.62 (s, 1H), 7.55 (t, J=8.0 Hz, 1H), 7.36-7.29 (m, 1H), 7.22-7.15 (m, 1H), 4.07 (s, 4H), 3.95 (s, 2H), 3.88 (t, J=6.8 Hz, 2H), 3.72 (s, 3H), 2.21 (t, J=6.8 Hz, 2H), 1.88 (s, 3H), 1.84 (s, 3H)

The calculated value of MS-ESI is [M+H]$^+$ 515 and 517, and the actual value is 515 and 517.

Embodiment 21

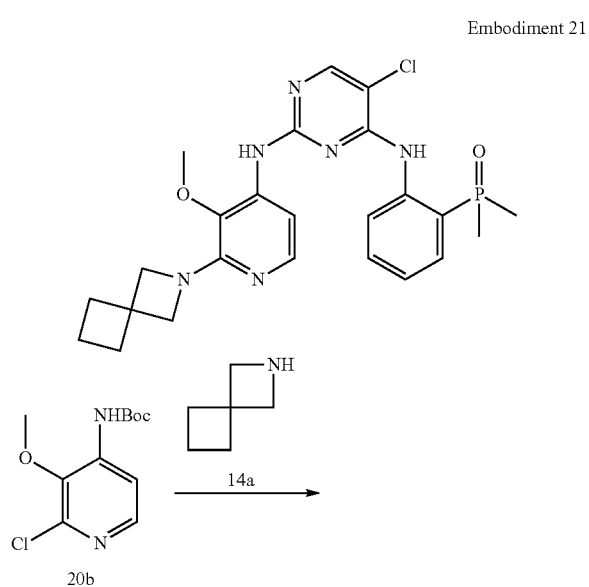

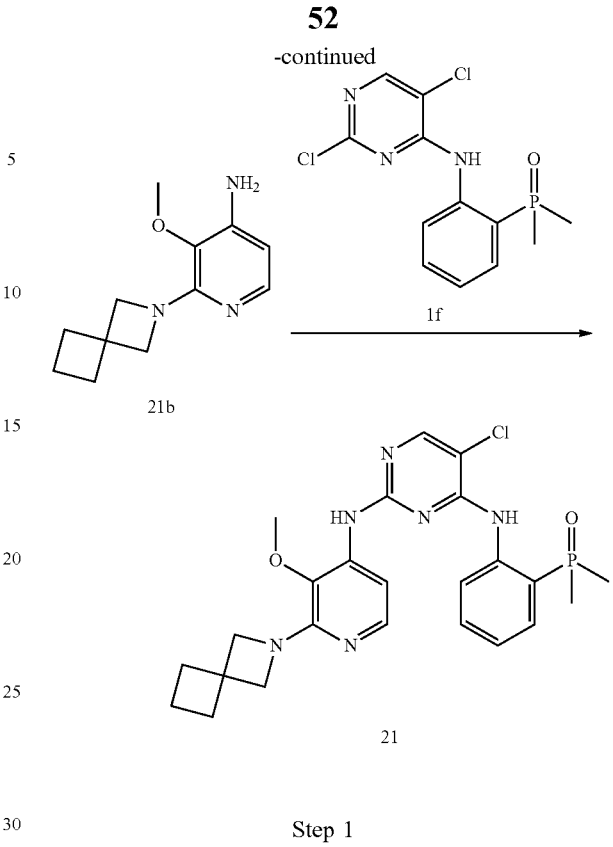

Step 1

Dissolve 20b (100 mg, 0.387 mmol), 14a (37.5 mg, 0.387 mmol), 1,1'-binaphthyl-2,2'-diphenyl phosphine (24.1 mg, 0.039 mmol) and sodium tert-butoxide (92.9 mg, 0.966 mmol) in 1,4-dioxane (2.00 mL). Add palladium acetate (3.4 mg, 0.023 mmol) to the reaction liquid with the protection of nitrogen, and stir the reaction liquid for 16 hours at 110° C. Add water (2 mL) and extract the reaction liquid with ethyl acetate (5 mL×3). Combine the organic phase, dry it with anhydrous sodium sulphate and filter it. Concentrate the filtrate under reduced pressure. Separate and purify the residues with preparation thin-layer chromatography to obtain 21a.

$^1$H NMR (400 MHz, CDCl$_3$) δ 7.83 (d, J=5.6 Hz, 1H), 7.45 (d, J=5.6 Hz, 1H), 7.12 (s, 1H), 4.01 (s, 4H), 3.66 (s, 3H), 2.20 (t, J=7.2 Hz, 4H), 1.91-1.83 (m, 2H), 1.53 (s, 9H)

Step 2

Dissolve 21a (55.0 mg, 0.172 mmol) in dichloromethane (3.0 mL). Add trifluoroacetic acid (1.0 mL) to the reaction liquid at 0° C., and stir the reaction liquid for 15 hours at 25° C. Directly concentrate the reaction liquid to obtain 21b.

The calculated value of MS-ESI is [M+H]$^+$ 220, and the actual value is 220.

Step 3

Dissolve 21b (36.9 mg, 0.111 mmol), 1f (35.0 mg, 0.111 mmol) and sodium tert-butoxide (42.6 mg, 0.443 mmol) in tetrahydrofuran (2.0 mL). Add (2-di-tert-butylphosphino-2',4',6'-triisopropyl-1,1'-biphenyl) (2'-amino-1,1'-biphenyl-2-yl) palladium (II) (4.4 mg, 0.0055 mmol) with the protection of nitrogen, and stir the reaction liquid for 16 hours at 90° C. Filter and steam the reaction liquid dry. Purify it with preparative high performance liquid chromatography to obtain 21.

¹H NMR (400 MHz, CDCl₃) δ 10.88 (s, 1H), 8.48 (dd, J=4.4, 8.4 Hz, 1H), 8.08 (s, 1H), 7.73-7.70 (m, 2H), 7.55 (s, 1H), 7.47 (t, J=8.0 Hz, 1H), 7.27-7.22 (m, 1H), 7.12-7.08 (m, 1H), 3.97 (s, 4H), 3.62 (s, 3H), 2.14 (t, J=7.8 Hz, 4H), 1.84-1.82 (m, 1H), 1.80 (s, 3H), 1.78-1.77 (m, 1H), 1.76 (s, 3H)

The calculated value of MS-ESI is [M+H]+ 499 and 501; the actual value is 499 and 501.

Embodiment 22

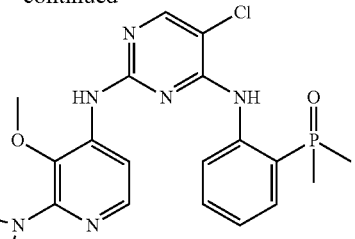

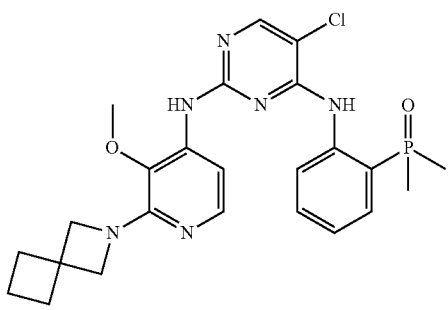

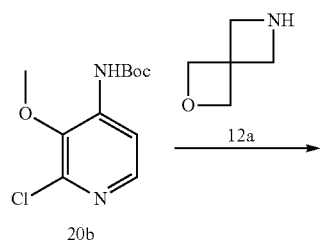

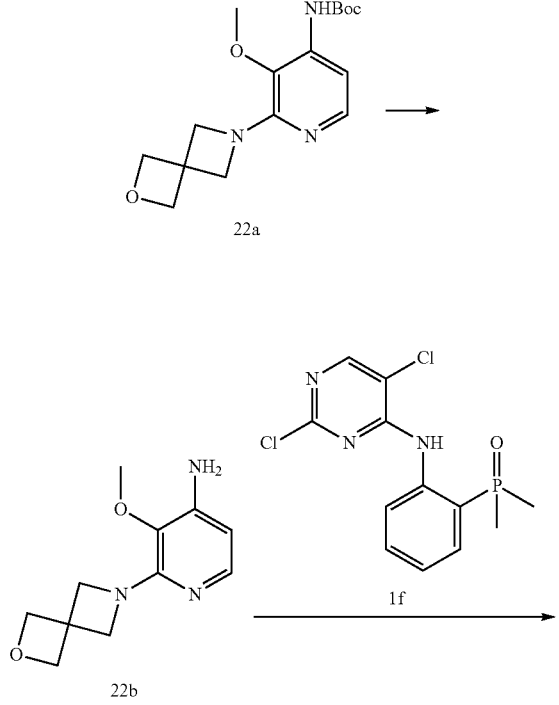

Step 1

Dissolve 21b (100 mg, 0.387 mmol), 12a (38.3 mg, 0.387 mmol), 1,1'-binaphthyl-2,2'-diphenyl phosphine (24.1 mg, 0.039 mmol) and sodium tert-butoxide (92.9 mg, 0.966 mmol) in 1,4-dioxane (2.00 mL). Add palladium acetate (3.4 mg, 0.023 mmol) to the reaction liquid with the protection of nitrogen, and stir the reaction liquid for 16 hours at 110° C. Add water (3 mL) and extract the reaction liquid with ethyl acetate (6 mL×3). Combine the organic phase, dry it with anhydrous sodium sulphate and filter it. Concentrate the filtrate under reduced pressure. Separate and purify the residues with preparation thin-layer chromatography to obtain 22a.

¹H NMR (400 MHz, CDCl₃) δ 7.84 (d, J=5.6 Hz, 1H), 7.51 (d, J=5.6 Hz, 1H), 7.12 (s, 1H), 4.85 (s, 4H), 4.21 (s, 4H), 3.66 (s, 3H), 1.54 (s, 9H).

Step 2

Dissolve 22a (100 mg, 0.311 mmol) in dichloromethane (3.0 mL). Add trifluoroacetic acid (1.0 mL) to the reaction liquid at 0° C., and stir the reaction liquid for 3 hours at 25° C. Directly concentrate the reaction liquid to obtain 22b.

The calculated value of MS-ESI is [M+H]⁺ 222, and the actual value is 222.

Step 3

Dissolve 22b (63.0 mg, 0.285 mmol), 1f (90.0 mg, 0.111 mmol) and sodium tert-butoxide (109 mg, 1.14 mmol) in tetrahydrofuran (2.0 mL). Add (2-di-tert-butylphosphino-2', 4',6'-triisopropyl-1,1'-biphenyl) (2'-amino-1,1'-biphenyl-2-yl) palladium (II) (11.3 mg, 0.014 mmol) with the protection of nitrogen, and stir the reaction liquid for 16 hours at 100° C. Filter and steam the reaction liquid dry. Purify it with preparative high performance liquid chromatography to obtain 22.

¹H NMR (400 MHz, CDCl₃) δ 10.98 (s, 1H), 8.55 (dd, J=4.4, 8.4 Hz, 1H), 8.16 (s, 1H), 7.88-7.83 (m, 1H), 7.82-7.76 (m, 1H), 7.61 (s, 1H), 7.55 (t, J=7.6 Hz, 1H), 7.35-7.30 (m, 1H), 7.20-7.16 (m, 1H), 4.86 (s, 4H), 4.24 (s, 4H), 3.70 (s, 3H), 1.87 (s, 3H), 1.84 (s, 3H)

The calculated value of MS-ESI is [M+H]⁺ 501 and 503, and the actual value is 501 and 503.

Experimental Embodiment: In Vitro Evaluation of LRRK2 Kinase Inhibitory Activity Experimental purpose: to detect transfer of energy signals (ratio of fluorescence signals: 520 nM/485 nM) after the phosphate group of phosphorylated Fluorescein-ERM (LRRKtide) peptide binds with LanthaScreen® Tb-pERM (pLRRKtide) antibody using homogeneous time-resolved fluorescence. Calculate $IC_{50}$ for LRRK2 inhibition of the compound to be assayed.

Experimental Materials

1. Reaction solution: 10 mM 4-(2-hydroxyethyl) piperazine-1-ethanesulfonic acid (pH 7.5); 2 mM magnesium chloride; 0.5 mM glycol-bis-(2-aminoethylether)-N; 0.002% primary alcohol ethoxylate, 1 mM dithiothreitol and 1% DMSO;
2. Assay solution: TR-FRET Dilution Buffer;
3. LRRK2 human recombinant protein: use GST tag and baculovirus to express LRRK2 full-length human recombinant protein in Sf9 cells of insects;
4. Substrate: 0.4 uM Fluorescein-ERM (LRRKtide) peptide; 57 uM ATR
Assay Methods:
HTRF;
Resonance energy transfer of Fluorescein-ERM (LRRKtide) peptide and LanthaScreen® Tb-pERM (pLRRKtide) antibody between 485 nM and 520 nM.

Experimental Operations

1. Add DMSO solution of the compound to be assayed through the Echo550 non-contact nano-liter acoustic droplet ejection system;
2. Prepare mixed solution of enzyme and polypeptide with freshly prepared reaction solution. Add the mixed solution to the reaction cavity and warm it up at room temperature for 20 minutes in advance;
3. Add 57 μM ATP to initiate reaction, which lasts for 90 minutes at room temperature;
4. Add fluorescein-ERM (LRRKtide) peptide, LanthaScreen® Tb-pERM (pLRRKtide) antibody and 10 mM ethylene diamine tetraacetic acid to the assay system. The reaction lasts for 60 minutes at room temperature. Detect yellow light signals with Em/Ex 520/485.
5. Measure enzyme activity inhibition relative to DMSO blank control group according to the signal ratio, and calculate $IC_{50}$ by fitting curves with the software XLfit5.

Experimental Results

TABLE 1

Test Results on Inhibitory Activity for LRRK2

| Specimens (Compounds Prepared in Each Embodiment) | Inhibitory Activity for LRRK2 (nM) |
|---|---|
| Embodiment 1 | 21.0 |
| Embodiment 2 | 24.4 |
| Embodiment 3 | 6.2 |
| Embodiment 4 | 34.2 |
| Embodiment 5 | 8.2 |
| Embodiment 6 | 2.9 |
| Embodiment 7 | 8.5 |
| Embodiment 8 | 7.2 |
| Embodiment 9 | 7.8 |
| Embodiment 10 | 21.6 |
| Embodiment 11 | 5.3 |
| Embodiment 12 | 1.6 |
| Embodiment 13 | 9.1 |
| Embodiment 14 | 15.2 |
| Embodiment 15 | 7.4 |
| Embodiment 16 | 10.6 |

TABLE 1-continued

Test Results on Inhibitory Activity for LRRK2

| Specimens (Compounds Prepared in Each Embodiment) | Inhibitory Activity for LRRK2 (nM) |
|---|---|
| Embodiment 17 | 27.7 |
| Embodiment 18 | 4.6 |
| Embodiment 19 | 11.9 |
| Embodiment 20 | 1.6 |
| Embodiment 21 | 36.8 |
| Embodiment 22 | 2.6 |

Experimental Embodiment: In Vitro Evaluation of Inhibitory Activity for LRRK2 Cell (pSer935)

Cell Preparation:
1. Cell Defrosting
Take 293T cells out of liquid nitrogen and put them in water at 37° C. After ice has fully thawed, transfer the cells to 5 mL warm culture medium. Discard the supernatant through centrifugation, and culture the suspended cells in the culture medium as new cells.
2. Cell Culture and Passage
Culture the 293T cells in the culture medium for two to three days.
3. Cell Freezing
Put the cultured cell strain into the fresh culture medium and dilute its concentration to 1*10^7. Then, mix it with an equal amount of culture medium. Equally divide it into several groups, with 1 mL in each group, and put them at −80° C. for one day. Then, transfer them to liquid nitrogen.

Experimental Procedures 1. (Day 1) 293T Cell Seeding
Plant 1.4×10^6/293T cells on a culture plate. After two days of culturing, cells will multiply to 5×10^6, so planting cells on N+1 plates is enough for performing experiments on N 96-well plates.
2. (Day 2) 293T Cell Transfection
1) Add 5 μl (0.5 μg/μl) pcmv-flag-Irrk2 to 145 μl DMEM culture medium, and mix them evenly with a straw;
2) Add 15 μl transfection reagent and mix them with a straw;
3) Keep them still for 10 minutes at room temperature;
4) Add 0.5 mL preheated cell culture medium and mix it evenly;
5) Add 650 μl mixture to the 6-well plate drop by drop and mix them thoroughly;
6) Incubate the culture plate inside a humidified incubator with 5% carbon dioxide for 20 to 24 hours at 37° C.
3. (Day 3) Plant the 293T Cells on the 96-Well Plate;
4. (Day 4) Inhibitor Treatment
1) Treat the compounds with a centrifugal machine;
2) Add 55 μl cell culture medium to the inhibitor plate. Preheat the plate at 37° C.
3) Transfer 50 μl inhibitor containing culture medium to the cell culture plate;
4) Incubate the culture plate inside a humidified incubator with 5% carbon dioxide for 20 to 24 hours at 37° C.;
5) Extract 300 μl inhibitor containing culture medium with a dropper. Take 200 μl inhibitor containing culture medium and add 100 μl decomposer into the culture medium. After the plate has been sealed, it shall be shaken for 30 minutes at 4° C.
6) Later, keep the plate at −20° C. until it is used.
5. (Day 5) MSD Procedures 1) Add 2 μg/25 μl labeled antibody to the MSD plate to incubate for 2 hours; (50 μl 3.9 μg/μl Flag antibody+2.5 ml fetal bovine serum per plate). Maintain centrifugation for 10 s (1,000 rpm);
2) Discard the labeled antibody, and slowly rinse several points twice using 300 μl wash buffer;
3) Add 50 μl buffer to each plate and incubate for 2 hours;
4) Discard the buffer and manually wash twice with 300 μl wash buffer;
5) Transfer 12.5 μl lysis buffer and 12.5 μl cell lysis buffer to the MSD plate to incubate for 1 hour at room temperature;
6) Discard the lysis buffer, and slowly rush several points three times with 300 μl wash buffer;
7) Dilute ps935 antibody at 1:200, and add 25 μl antibody to incubate for 1 hour;
8) Discard the primary antibody, and slowly rush several points three times with 300 μl wash buffer;
9) Dilute goat anti-rabbit antibody at 1:500, and add 25 μl antibody to the incubation plate to incubate for 1 hour;
10) Discard the secondary antibody, and slowly rush several points three times with 300 μl wash buffer. The wash buffer finally flows to the MSD reader;
11) Collect data twice;
12) Discard the final wash buffer, and add 150 μl/twice the buffer to the well plate to be read;
13) After incubation for about 3 minutes, read data over 15 minutes.

Experimental Results

TABLE 2

Test Results on Inhibitory Activity for pSer935 Cell

| Specimens (Compounds Prepared in Each Embodiment) | Inhibitory Activity for pSer935 Cell (nM) |
| --- | --- |
| Embodiment 3 | 4.3 |
| Embodiment 5 | 4.0 |
| Embodiment 6 | 3.3 |
| Embodiment 7 | 10.9 |
| Embodiment 9 | 4.7 |
| Embodiment 11 | 4.5 |
| Embodiment 12 | 3.7 |
| Embodiment 18 | 86.1 |
| Embodiment 20 | 22.0 |
| Embodiment 22 | 44.0 |

Conclusion: The compounds in this invention have potent effects for inhibiting LRRK2 and pSer935 activity.

Experimental Embodiment 3: Pharmacokinetic Evaluation of the Compounds

Experimental purpose: to study pharmacokinetics of the compounds in vivo in C57BL/6 mice—drug concentration ratio between brain tissues and plasma
Experimental materials: C57BL/6 mice (male, 8 weeks old, weight: 25 g-30 g)

Experimental Operations

Assay Pharmacokinetic Features of Glires after they are Orally Administered the Compounds According to Standard Schemes.

In the experiment, the candidate compounds are prepared into 1 mg/mL mixed suspension, and mice are orally administered once. The menstruum for oral administration is 10% dimethyl sulfoxide (DMSO)/10% polysorbate/20% PEG-400 aqueous solution. This project uses male C57BL/6 mice, which are orally administered drugs at a dose of 5 mg/kg. Collect the whole brain 0.5, 1, 2 and 4 hours after the administration. Homogenize tissue samples with 15 mM [fetal bovine serum (pH=7.4) buffer and methanol (volume ratio: 2:1)] at a ratio of 1:5 (w:v). Equally divide the homogenate into 2 samples: one for assay and the other for standby use. Besides, collect plasma 0.5, 1, 2 and 4 hours after administration. Centrifugate with 3,000 g relative centrifugal force within half an hour after collection at about 4° C. for 15 minutes to separate supernatant and obtain plasma samples. Store the plasma samples in polypropylene tubes; rapidly freeze them on dry ice and keep them at −80° C. till LC/MS/MS assay. Add internal standard precipitated protein of acetonitrile solution and fully mix them to extract supernatant samples via centrifugation. Quantitatively analyze plasma concentration by LC-MS/MS assay and calculate pharmacokinetic parameters such as maximal concentration ($C_{max}$), half-life ($T_{1/2}$), maximal time ($T_{max}$), drug concentration in different tissues after administration ($AUC_{0\text{-}last}$), and drug concentration ratio between brain tissues and plasma (B/P). For the Embodiments of this invention, the pharmacokinetic parameters in vivo in mice are shown in Table 3 as follows.

TABLE 3

In Vivo Pharmacokinetic Assay Results

| | $C_{max}$ (nM) | | Tmax (h) | | $T_{1/2}$ (h) | | $AUC_{0\text{-}last}$ (nM · hr) | | |
| --- | --- | --- | --- | --- | --- | --- | --- | --- | --- |
| Specimens | Brain Tissues | Plasma | Brain Tissues | Plasma | Brain Tissues | Plasma | Brain Tissues | Plasma | (B/P) |
| Embodiment 3 | 217 | 1181 | 0.5 | 0.5 | Undetected | 0.59 | 192 | 1386 | 0.14 |
| Embodiment 9 | 604 | 2603 | 0.50 | 0.50 | 0.36 | 0.56 | 489 | 2479 | 0.20 |
| Embodiment 11 | 698 | 1557 | 0.50 | 0.50 | 0.37 | 0.47 | 597 | 1447 | 0.41 |
| Embodiment 12 | 576 | 3627 | 0.50 | 0.50 | 0.39 | 0.60 | 476 | 3459 | 0.14 |
| Embodiment 13 | 726 | 1197 | 0.5 | 0.5 | 0.72 | 0.98 | 1164 | 2250 | 0.52 |

TABLE 3-continued

In Vivo Pharmacokinetic Assay Results

| Specimens | $C_{max}$ (nM) | | Tmax (h) | | $T_{1/2}$ (h) | | $AUC_{0-last}$ (nM · hr) | | (B/P) |
| --- | --- | --- | --- | --- | --- | --- | --- | --- | --- |
| | Brain Tissues | Plasma | Brain Tissues | Plasma | Brain Tissues | Plasma | Brain Tissues | Plasma | |
| Embodiment 14 | 2042 | 1650 | 1.0 | 1.0 | Undetected | Undetected | 4200 | 4392 | 0.96 |
| Embodiment 15 | 1436 | 2147 | 0.5 | 0.5 | 0.63 | 0.75 | 2151 | 4019 | 0.54 |

Conclusion: The compounds in this invention exhibit ideal in vivo pharmacokinetic natures, including desirable drug concentration in brain tissues and B/P.

Experimental Embodiment 4: In Vivo Pharmacological Experiment

Experimental purpose: to assay effects of the compounds for inhibiting LRRK2 phosphorylation in brain tissues of mice and LRRK 2 and Rab10 phosphorylation in peripheral blood mononuclear cells (PBMC).

Experimental Materials

Animals: C57BL/6J mice (male, 6-7 weeks old, weight: 20 g-22 g).

Experimental Procedures

1. Grouping: Weigh all mice one day ahead of the experiment and divide them into 6 groups at random according to their weight, with 4 mice in each group. Exclude too heavy and too light mice, to ensure that average weight of all groups is the same. The grouping is shown in Table 4 as follows. There are 6 groups altogether, including blank control group (Group 1, n=4, menstruum), positive control group (Group 2-3, n=4, GNE-7915 and MLi-2), and drug Embodiment 11 (Group 4-6, n=4, 11).

TABLE 4

Grouping and Dose

| Group | Specimens | Quantity | Administration Method | Concentration mg/mL | Dose mg/kg | Dosing Frequency |
| --- | --- | --- | --- | --- | --- | --- |
| 1 | Menstruum | 4 | Oral Intragastrical Administration | N/A | N/A | Once |
| 2 | GNE-7915 | 4 | Oral Intragastrical Administration | 1 | 10 | Once |
| 3 | MLi-2 | 4 | Oral Intragastrical Administration | 1 | 10 | Once |
| 3 | Embodiment 11 | 4 | Oral Intragastrical Administration | 0.3 | 3 | Once |
| 4 | Embodiment 11 | 4 | Oral Intragastrical Administration | 1 | 10 | Once |
| 5 | Embodiment 11 | 4 | Oral Intragastrical Administration | 3 | 30 | Once |

Menstruum: 10% dimethyl sulfoxide (DMSO)/10% polysorbate/20% PEG-400 aqueous solution.

2. Experimental Operations 2.1 Administration and Tissue Collection

The animals of each group are orally administered menstruum or the compound to be assayed in chronological order as shown in Table 4. One mouse is administered every 2 minutes. 1 hour after administration, all animals are successively euthanized with carbon dioxide in chronological order. Collect 600 µl whole blood by heart puncture and place it in an EDTA-K2 containing anticoagulation tube. Take 100 µl whole blood for centrifugation for 10 minutes at 4° C. and 8,000 rpm to separate plasma and freeze it in liquid nitrogen. Subsequently, transfer the plasma to dry ice for further research. Separate peripheral blood mononuclear cells (PBMC) from the remained blood through density gradient centrifugation using cell separation solution. Meanwhile, collect brain, lung and kidney tissues from the animals. Quickly freeze and place them in dry ice. Then, transfer them for preservation at −80° C.

2.2 Separation of PBMC

Add fetal bovine serum (1 mL, twice the volume) to the remained blood sample of each group (500 µl) for dilution, and gently mix them. Add 3 mL separation solution to a 50 mL centrifugal tube, and gently add the diluted blood sample to the supernatant of the centrifugal liquid. Centrifugate with 800 g relative centrifugal force for 20 minutes at room temperature. Both the ascending and descending speed is 0. At the end of centrifugation, there will be three layers: the upper layer with plasma, the middle layer with separation solution and the lower layer with red blood cells. Between the plasma and separation solution is a mist layer. Gently suck the mist layer out and place it into another 15 mL centrifugal tube. Add fetal bovine serum to dilute till 8 mL and centrifugate with 800 g relative centrifugal force at 4° C. for 5 minutes. Discard the supernatant and ensure that all supernatant is sucked out. Add 1 mL ACK cell lysis buffer to each tube, and keep them at room temperature for 10 minutes. 10 minutes later, add fetal bovine serum to each tube till the volume reaches 10 mL and mix them evenly. Centrifugate with 800 g relative centrifugal force at 4° C. for 5 minutes. Discard the supernatant. Add 1 mL fetal bovine serum for resuspension, and mix them evenly. Suck 50 μl cell solution out and add 450 μl fetal bovine serum to the solution for cell counting. After counting cells of all samples, centrifuge with 800 g relative centrifugal force at 4° C. for 5 minutes. Discard the supernatant and insert the cells into dry ice for quick freezing. Subsequently, store the cells in a refrigerator at −80° C.

2.3 Pharmacological Assay (1) After protein determination of brain tissue samples by BCA, apply 4% to 15% precast gel in an equal amount of protein samples.

(2) Add SDS Lysis Buffer according to PBMC count, and apply 13 μl to 4-15% precast glue in all samples.

(3) Perform protein electrophoresis at 200 V for 30 minutes. Then, use Midi PVDF Transfer Packs for membrane transfer for 7 minutes. Next, block them with TBS Blocker at room temperature for 1 hour.

(4) Prepare 5% milk with skimmed milk powder. Then, formulate antibodies P-LRRK2 (add 20 μl antibody to 5 mL 5% milk at 1:250), total-LRRK2 (add 10 μl antibody to 5 ml 5% skimmed milk at 1:500), p-Rab10 (add 10 μl antibody to 5 mL 5% skimmed milk at 1:500) and p-actin (add 5 μl antibody to 5 mL 5% milk at 1:1000), and incubate the antibodies overnight.

(5) Recycle the primary antibodies and rinse membranes with TBS for three times, 10 minutes each time.

(6) Block secondary anti-rabbit antibodies (add 5 μl antibody to 10 mL 5% milk at 1:2000) at room temperature for one hour, and wash the membranes for 3 times with TBS. Then, render the bands colors.

3. Experimental Results 3.1 Western Blot Results on Immunity of Brain Tissues (FIG. 1)

Figure 2:
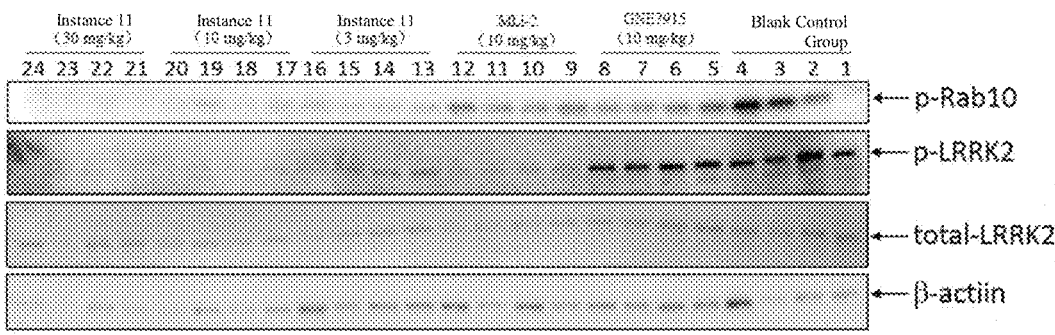

3.2 Western Blot Results on Immunity of PBMC (FIG. 2)

Conclusions: The compounds in this invention have potential effects for inhibiting FRRK2 phosphorylation in brain tissues of mice. In addition, its inhibitory effects tend to be dose dependent at 3 mg/kg, 10 mg/kg and 30 mg/kg. When dosed at 3 mg/kg, the compound in this invention inhibits FRRK2 phosphorylation to the same degree as GNE-7915 (reference compound) inhibits FRRK2 phosphorylation at a dose of 10 mg/kg. The compound in this invention significantly inhibits phosphorylation of FRRK2 and its downstream protein Rab10. When dosed at 3 mg/kg, 10 mg/kg and 30 mg/kg, it tends to be dose-dependent in inhibiting FRRK2 phosphorylation. Furthermore, the compound in this invention, when dosed at 10 mg/kg, outperforms GNE-7915 (reference compound) in inhibiting FRRK2 and Rab10 phosphorylation.

The invention claimed is:

1. A compound of formula (I) or a pharmaceutically acceptable salt thereof,

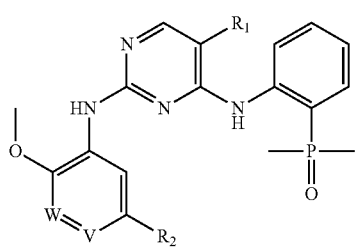

(I)

Wherein:
$R_1$ is selected from halogen, OH, $NH_2$ and $C_{1-6}$ alkyl, wherein $C_{1-6}$ alkyl is optionally substituted by 1, 2 or 3 $R_a$ radicals;
W is selected from N, and V is selected from $C(R_3)$;
or W is selected from $C(R_3)$, and V is selected from N;
$R_2$ is selected from H, and $R_3$ is selected from

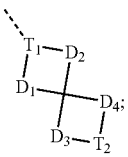

or $R_2$ is selected from

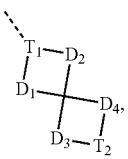

and R3 is selected from H;
$T_1$ is selected from N and CH;
$T_2$ is selected from —O—, —$CH_2$— and —$CH_2CH_2$—, wherein —$CH_2$— is optionally substituted by 1 or 2 $R_b$ radicals; —$CH_2CH_2$— is optionally substituted by 1, 2 or 3 $R_b$ radicals;
$D_1$ and $D_2$ are separately selected from single bonds, —$CH_2$— and —$CH_2CH_2$—, wherein —$CH_2$— is optionally substituted by 1 or 2 $R_c$ radicals; —$CH_2CH_2$— is optionally substituted by 1, 2 or 3 $R_c$ radicals; $O_1$ and $O_2$ are not simultaneously selected from single bonds;
$D_3$ and $D_4$ are separately selected from single bonds, —O—, —$CH_2$— and —$CH_2CH_2$—, wherein —$CH_2$— is optionally substituted by 1 or 2 $R_d$ radicals, —$CH_2CH_2$— is optionally substituted by 1, 2 or 3 $R_d$ radicals, $D_3$ and $D_4$ are not simultaneously selected from single bonds;
$R_a$ is separately selected from F, Cl, Br, I, OH and $NH_2$;
$R_b$ is separately selected from F, Cl, Br, I, OH and $NH_2$;
$R_c$ is separately selected from F, Cl, Br, I, OH and $NH_2$;
$R_d$ is separately selected from F, Cl, Br, I, OH, $NH_2$, $C_{1-6}$ alkyl and $C_{1-6}$ heteroalkyl, wherein $C_{1-6}$ alkyl and $C_{1-6}$ heteroalkyl are optionally substituted by 1, 2 or 3 R radicals;
R is separately selected from F, Cl, Br, I, OH and $NH_2$;
$C_{1-6}$ alkyl contains 1, 2 or 3 heteroatoms and heteroatom clusters of —O—, —S— and —NH—.

2. The compound of claim 1 or a pharmaceutically acceptable salt thereof, wherein $R_1$ is selected from F, Cl, Br, I, OH, $NH_2$ and $C_{1-3}$ alkyl; wherein $C_{1-3}$ alkyl is optionally substituted by 1, 2 or 3 $R_a$ radicals.

3. The compound of claim 2 or a pharmaceutically acceptable salt thereof, wherein $R_1$ is selected from F, Cl, Br, I, OH, $NH_2$ and $CF_3$.

4. The compound of claim 1 or a pharmaceutically acceptable salt thereof, wherein $D_1$ and $D_2$ are separately selected from single bonds, —$CH_2$— and —$CH_2CH_2$—; $D_1$ and $D_2$ are not simultaneously selected from single bonds.

5. The compound of claim 1 or a pharmaceutically acceptable salt thereof, wherein $R_d$ is separately selected from F, Cl, Br, I, OH, $NH_2$, $C_{1-3}$ alkyl and $C_{1-3}$ oxyalkyl, wherein $C_{1-3}$ alkyl and $C_{1-3}$ oxyalkyl are optionally substituted by 1, 2 or 3 R radicals.

6. The compound of claim 5 or a pharmaceutically acceptable salt thereof, wherein $R_d$ is separately selected from F, Cl, Br, I, OH, $NH_2$, $C_{1-3}$ alkyl and $C_{1-3}$ oxyalkyl.

7. The compound of claim 6 or a pharmaceutically acceptable salt thereof, wherein $R_d$ is separately selected from F, Cl, Br, I, OH, $NH_2$, Me, $CF_3$ and

8. The compound of claim 1 or a pharmaceutically acceptable salt thereof, $D_3$ and $D_4$ are separately selected from single bonds, —O—, —$CH_2$—, —$CF_2$—, —$CH_2CF_2$— and

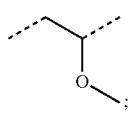

D3 and D4 are not simultaneously selected from single bonds.

9. The compound of claim 1 or a pharmaceutically acceptable salt thereof,

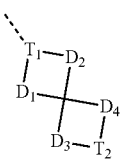

is selected from,

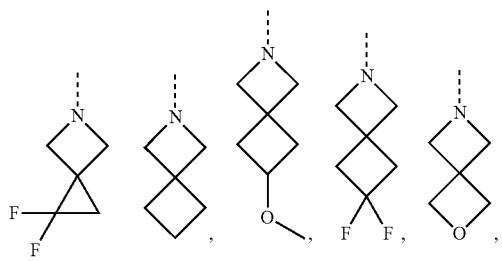

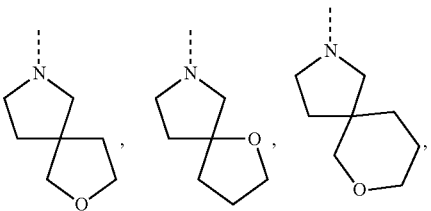

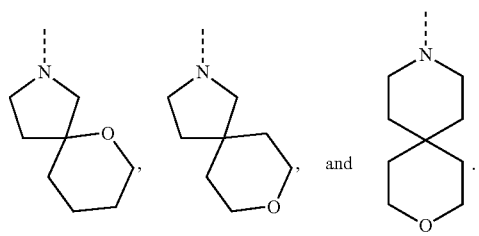

10. The compound of claim 1 or a pharmaceutically acceptable salt thereof, the compound or salt is selected from is selected from

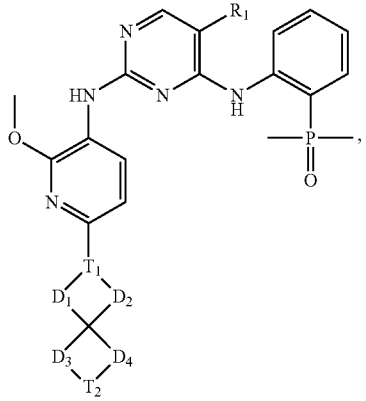

(I-1)

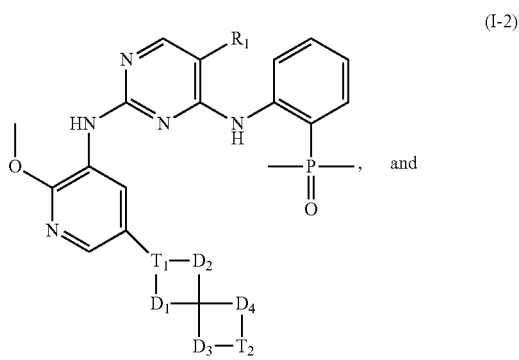

(I-2)

and

-continued
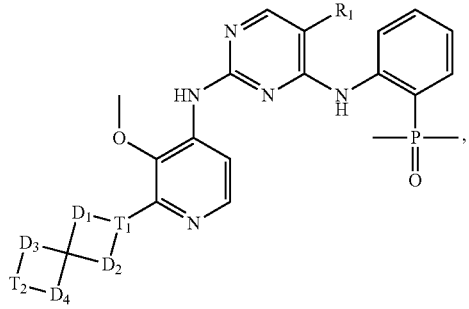
(I-3)
wherein:
R₁, T₁, T₂, D₁, D₂, D₃ and D₄ have the meanings as defined in claim 1.
11. A compound selected from the following formulas or a pharmaceutically acceptable salt thereof,
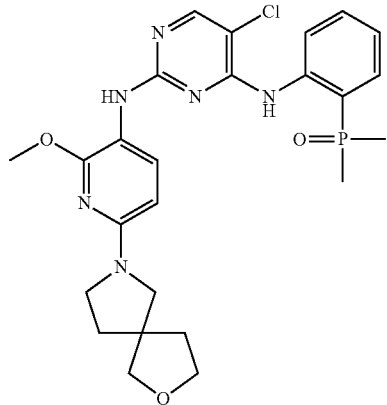
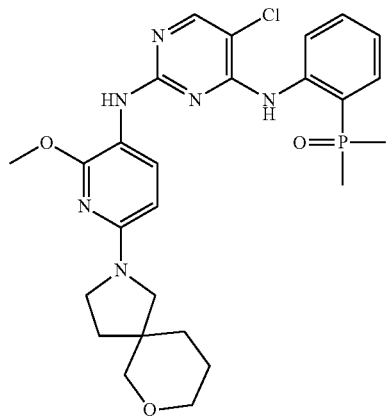
-continued
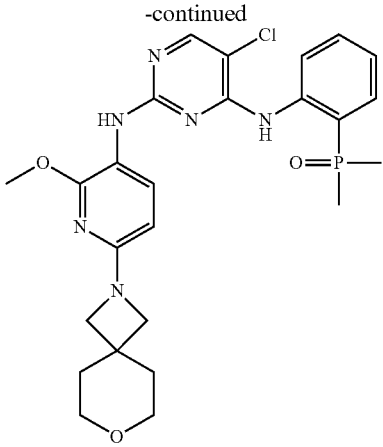
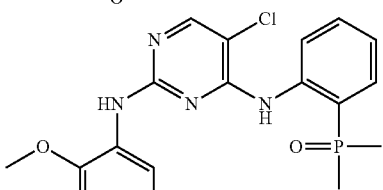
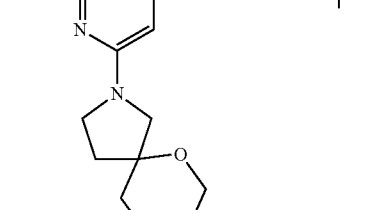
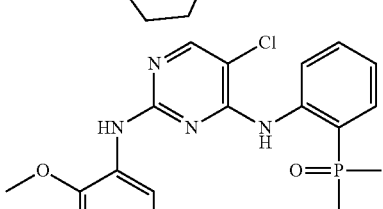
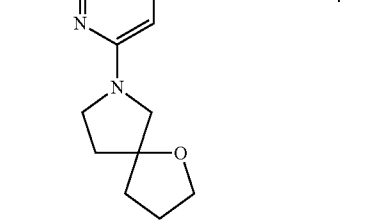
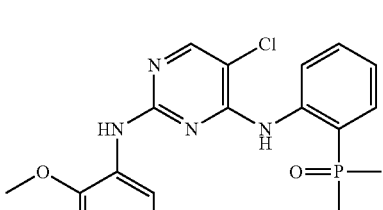
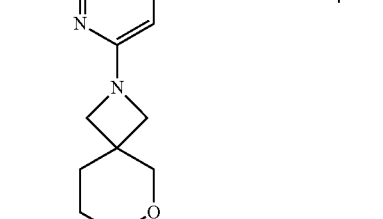

-continued
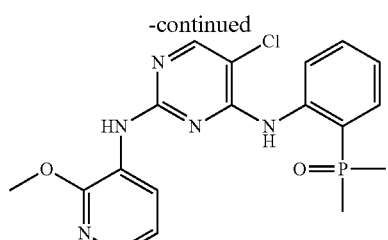
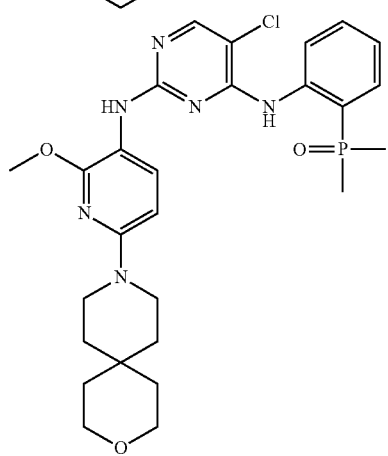
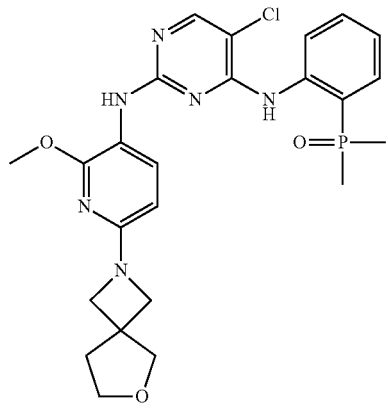
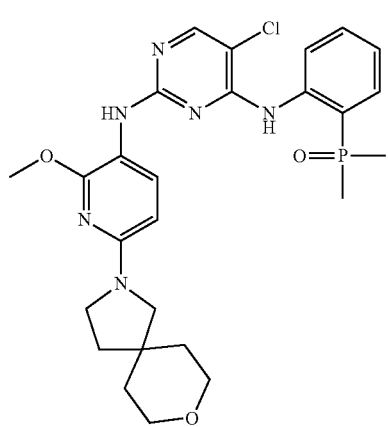
-continued
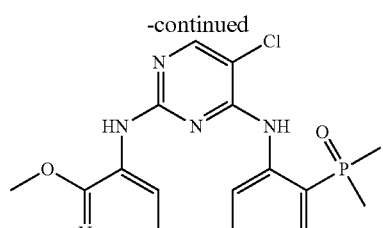
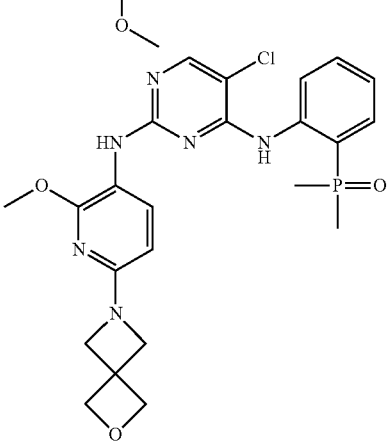
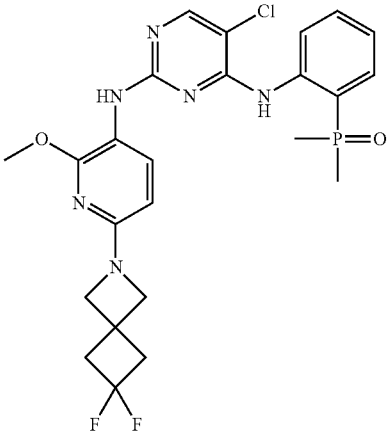
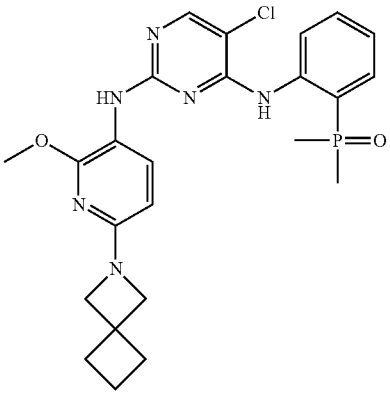

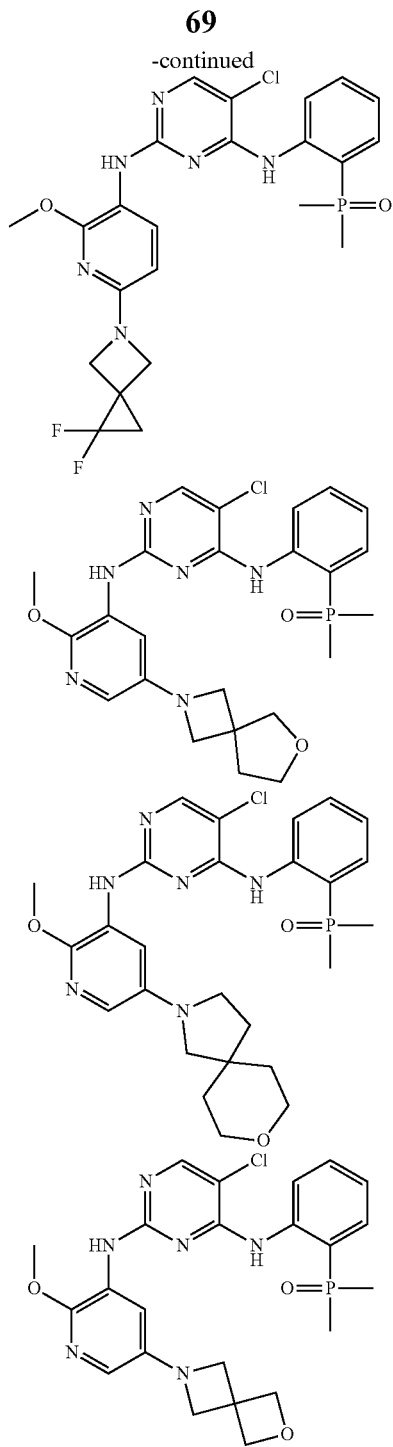
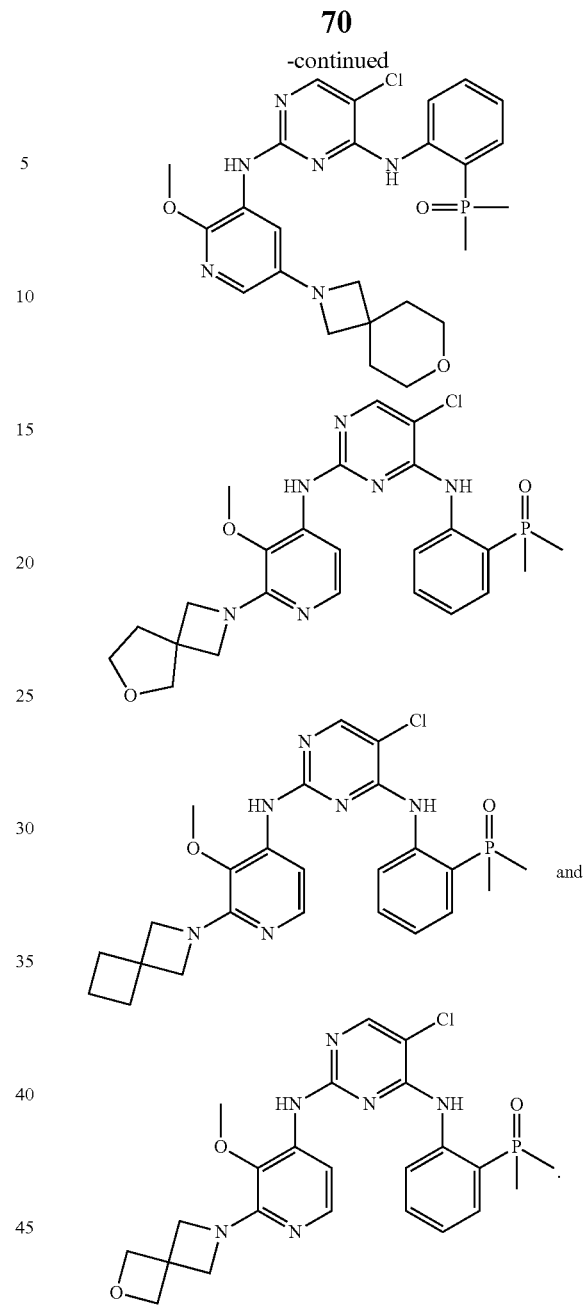
12. A compound of claim 1 or a pharmaceutically acceptable salt thereof for use in preparing a LRRK$_2$ kinase activity inhibitor-related drug.
* * * * *